US011020495B2

(12) United States Patent
MacDonald et al.

(10) Patent No.: US 11,020,495 B2
(45) Date of Patent: *Jun. 1, 2021

(54) HUMANIZED LOW AFFINITY FCγR MOUSE CELLS

(71) Applicant: Regeneron Pharmaceuticals, Inc., Tarrytown, NY (US)

(72) Inventors: Lynn MacDonald, Harrison, NY (US); Naxin Tu, Pleasantville, NY (US); Cagan Gurer, Chappaqua, NY (US); Sean Stevens, Del Mar, CA (US); Andrew J. Murphy, Croton-On-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/530,336

(22) Filed: Aug. 2, 2019

(65) Prior Publication Data

US 2020/0061213 A1    Feb. 27, 2020

Related U.S. Application Data

(60) Continuation of application No. 15/601,363, filed on May 22, 2017, now Pat. No. 10,426,848, which is a continuation of application No. 14/800,253, filed on Jul. 15, 2015, now Pat. No. 9,687,566, which is a continuation of application No. 14/152,106, filed on Jan. 10, 2014, now Pat. No. 9,089,599, which is a division of application No. 13/466,225, filed on May 8, 2012, now Pat. No. 8,658,853, which is a continuation of application No. 12/971,080, filed on Dec. 17, 2010, now Pat. No. 8,658,154.

(60) Provisional application No. 61/288,562, filed on Dec. 21, 2009.

(51) Int. Cl.
| | | |
|---|---|---|
| *A01K 67/027* | (2006.01) | |
| *A61K 49/00* | (2006.01) | |
| *C07K 14/735* | (2006.01) | |
| *G01N 33/50* | (2006.01) | |

(52) U.S. Cl.
CPC ...... *A61K 49/0008* (2013.01); *A01K 67/0276* (2013.01); *A01K 67/0278* (2013.01); *C07K 14/70535* (2013.01); *G01N 33/5014* (2013.01); *A01K 2207/15* (2013.01); *A01K 2217/072* (2013.01); *A01K 2217/075* (2013.01); *A01K 2217/15* (2013.01); *A01K 2227/105* (2013.01); *A01K 2267/03* (2013.01); *A01K 2267/0387* (2013.01)

(58) Field of Classification Search
USPC ................... 435/325; 800/3, 8, 18
See application file for complete search history.

(56) References Cited

U.S. PATENT DOCUMENTS

| | | | |
|---|---|---|---|
| 5,658,853 | A | 8/1997 | Kassebaum et al. |
| 5,859,312 | A | 1/1999 | Littman et al. |
| 5,877,396 | A | 3/1999 | Ravetch et al. |
| 6,111,166 | A | 8/2000 | van de Winkel |
| 6,294,347 | B1 | 9/2001 | Peltz et al. |
| 6,676,927 | B1 | 1/2004 | Ravetch |
| 7,265,261 | B2 | 9/2007 | Takai et al. |
| 7,309,810 | B2 | 12/2007 | Takai et al. |
| 7,351,875 | B2 | 4/2008 | Hogarth et al. |
| 7,402,728 | B2 | 7/2008 | Chan et al. |
| 7,579,170 | B2 | 8/2009 | Beliard et al. |
| 7,713,524 | B2 | 5/2010 | Bourel et al. |
| 8,658,154 | B2 * | 2/2014 | MacDonald ........ A61K 49/0008 424/93.2 |
| 8,658,853 | B2 * | 2/2014 | Macdonald ........ G01N 33/5014 800/18 |
| 8,883,496 | B2 * | 11/2014 | MacDonald ........ A01K 67/0278 435/325 |
| 9,056,130 | B2 * | 6/2015 | Macdonald ...... C07K 14/70535 |
| 9,089,599 | B2 * | 7/2015 | Macdonald ........ A01K 67/0278 |
| 9,221,894 | B2 * | 12/2015 | Macdonald ...... G01N 33/56977 |
| 9,687,566 | B2 * | 6/2017 | Macdonald ........ A01K 67/0276 |
| 10,426,848 | B2 * | 10/2019 | MacDonald ....... A01K 67/0276 |

(Continued)

FOREIGN PATENT DOCUMENTS

| | | | |
|---|---|---|---|
| EP | 3336102 A2 | 6/2018 | |
| WO | WO-1995028959 A1 | 11/1995 | |

(Continued)

OTHER PUBLICATIONS

Alevy, Y. et al., "CD32A (FcgRIIA) mRNA expression and regulation in blood monocytes and cell lines," Molecular Immunology, 29(11):1289-1297 (1992).

Allen, J. et al., "Isolation and Expression of Functional High-Affinity Fc Receptor Complementary DNAs," Science, 243:378-381 (1989).

Anderson, C., "Isolation of the receptor for IgG from a human monocyte cell line (U937) and from human peripheral blood monocytes," Journal of Experimental Medicine, 156:1794-1805 (1982).

(Continued)

*Primary Examiner* — Michael C Wilson
(74) *Attorney, Agent, or Firm* — Foley Hoag LLP; Brendan T. Jones

(57) ABSTRACT

Genetically modified non-human animals and methods and compositions for making and using them are provided, wherein the genetic modification comprises a deletion of the endogenous low affinity FcγR locus, and wherein the mouse is capable of expressing a functional FcRγ-chain. Genetically modified mice are described, including mice that express low affinity human FcγR genes from the endogenous FcγR locus, and wherein the mice comprise a functional FcRγ-chain. Genetically modified mice that express up to five low affinity human FcγR genes on accessory cells of the host immune system are provided.

33 Claims, 11 Drawing Sheets

Specification includes a Sequence Listing.

(56) References Cited

U.S. PATENT DOCUMENTS

| | | |
|---|---|---|
| 2004/0154044 A1 | 8/2004 | Fraichard et al. |
| 2006/0179501 A1 | 8/2006 | Chan et al. |
| 2008/0003225 A1 | 1/2008 | Vie et al. |
| 2009/0098124 A1 | 4/2009 | Stavenhagen |
| 2011/0142857 A1 | 6/2011 | Melamed et al. |

FOREIGN PATENT DOCUMENTS

| | | |
|---|---|---|
| WO | WO-9824893 A2 | 6/1998 |
| WO | WO-02/06630 A1 | 1/2002 |
| WO | WO-2004060052 A2 | 7/2004 |
| WO | WO-2009076464 A2 | 6/2009 |
| WO | WO-2011/084664 A1 | 7/2011 |

OTHER PUBLICATIONS

Anselmino, L. et al., "Human basophils selectively express the FcgRII (CDw32) subtype of IgG receptor," Journal of Allergy and Clinical Immunology, 84:907-914 (1989).
Barnes, N. et al., "FcgRI-Deficient Mice Show Multiple Alterations to Inflammatory and Immune Responses," Immunity,16:379-389 (2002).
Binstadt et al., "IgG Fc Receptor Polymorphisms in human disease: Implications for Intravenous Immunoglobulin Therapy," J Allergy and Clinical Immun, 111(4): 697-703.
Bolland, S., "A Newly Discovered Fc Receptor that Explains IgG-Isotype Disparities in Effector Responses," Immunity, 23:2-4 (2005).
Boros P. et al., "Fc Receptors" Encyclopedia of Life Sciences, pp. 1-8 (2008).
Breunis et al., "Copy Number Variation at the FCGR Locus Includes FCGR3A. FCGR2C and FCGR3B but not FCGR2A and FCGR2B," Human Mutation, 30(5):E640-650 (2009).
Brooks, D. et al., "Structure and expression of human IgG FcRII (CD32): Functional Heterogeneity Is Encoded by the Alternatively Spliced Products of Multiple Genes," Journal of Experimental Medicine,170:1369-1385 (1989).
Cassatella, M. et al., "FcgR(CD16) interaction with ligand induces Ca2+ mobilization and phosphoinositide turnover in human natural killer cells: Role of Ca2+ in FcgR(CD16)-induced transcription and expression of lymphokine genes," Journal of Experimental Medicine, 169:549-567 (1989).
Chu et al., "Association of Fcgamma Receptor IIb Polymorphism with Susceptibility to Systemic Lupus Erythematosus in Chinese: A Common Susceptibility Gene in the Asian Populations," Tiger Antigens, 63(1): 21-27 (2004).
Coggeshall, K., "Inhibitory signaling by B cell FcgRIIb," Current Opinion in Immunology, 10:308-312 (1998).
Cohen-Solal, J. et al., "Fc g receptors," Immunology Letters, 92:199-205 (2004).
Cowan et al., "Targeting gene expression to endothelium in transgenic animals: a comparision of the human ICAM-2, PECAM-1 and endoglin promoters," Xenotransplantation, 10: 223-231 (2003).
Deo, Y. et al., "Clinical significance of IgG Fc receptors and Fc gamma R-directed immunotherapies," Immunology Today,18(3):127-135 (1997).
Deonarain, "Ligand-targeted receptor-mediated vectors for gene delivery," Expert Opin. Ther. Pat., 8:53-69 (1998).
Desjarlais, J. et al., "Optimizing engagement of the immune system by anti-tumor antibodies: an engineer's perspective," Drug Discovery Today, 12(21-22):898-910 (2007).
Desoize, B., "Antibodies in cancer treatment," Critical Reviews in Oncology/Hematology, 62:23-25 (2007).
Dombrowicz et al., "Anaphylaxis mediated through a humanized high affinity IgE receptor," J Immunol, 157:1645-1651 (1996).
Ebert et al., "A Moloney MLV-Rat Somatotropin Fusion Gene Produces Biologically Active Somatotropin in a Transgenic Pig," Mol. Endocrinology, 2: 277-283 (1988).

Edelstein et al., "Gene therapy clinical trials worldwide 1989-2004— an overview," J. Gene Med., 6: 597-602 (2004).
Extended European Search Report for EP Application No. 18154933 dated Jun. 29, 2018.
Extended European Search Report for EP Application No. 19154880.9 dated Mar. 21, 2019.
Fleit, H. et al., "Human neutrophil Fcg receptor distribution and structure," PNAS, 79:3275-3279 (1982).
Fung-Leung et al., "Transgenic Mice Expressing the Human High-Affinity Immunoglobulin (Ig) E Receptor α Chain Respond to Human IgE in Mast Cell Degranulation and in Allergic Reactions," J Exp Med, 183:49-56 (1996).
Gessner, J. et al., "The IgG Fc receptor family," Annals of Hematology, 76:231-248 (1998).
Getahun, A. et al., "How antibodies act as natural adjuvants," Immunology Letters, 104:38-45 (2006).
Griggs, J. et al., "The state of the art: immune-mediated mechanisms of monoclonal antibodies in cancer therapy," British Journal of Cancer, 101:1807-1812 (2009).
Guyre, P. et al., "Increased potency of Fc-receptor-targeted antigens," Cancer Immunology and Immunotherapy, 45:146-148 (1997).
Haas, M., "IgG-Fc receptors and the clinical relvance of their polymorphisms," Wiener Klinische Wochenschrift, 113(20-21):825-831 (2001).
Hammer et al., "Spontaneous Inflammatory Disease in Transgenic Rats Expressing HLA-B27 and Human B2m: An Animal Model of HLA-B27-Associated Human Disorders," Cell, 63:1099-1112 (1990).
Hazenbos, W. et al., "Impaired IgG-Dependent Anaphylaxis and Arthus Reaction in FcgRIII (CD16) Deficient Mice," Immunity, 5:181-188 1996).
Heijnen, I. et al., "A Human FcgRI/CD64 Transgenic Model for In Vivo Analysis of (Bispecific) Antibody Therapeutics," Journal of Hematotherapy, 4:351-356 (1995).
Heijnen, I. et al., "Antigen Targeting to Myeloid-specific Human FcgRI/CD64 Triggers Enhanced Antibody Responses in Transgenic Mice," Journal of Clinical Investigation, 97(2):331-338 (1996).
Heijnen, I. et al., "Human IgG Fc Receptors," International Reviews in Immunology, 16:29-55 (1996).
Heyman, B., "Regulation of Antibody Responses via Antibodies, Complement, and Fc Receptors," Annual Reviews in Immunology, 18:709-737 (2000).
Hibbs, M. et al., "Molecular cloning of a human immunoglobulin G Fc receptor," PNAS, 85:2240-2244 (1988).
Hogarth, P. Fc receptors are major mediators of antibody based inflammation in autoimmunity. Current Opinion in Immunology 2002, 14:798-802.
Hulett, M. et al. Molecular Basis of Fc Receptor Function. Advances in Immunology 1994, 57:1-127.
International search report for PCT application No. PCT/US2010/060925, dated Mar. 14, 2011.
Johnson-Saliba, "Gene Therapy: Optimising DNA Delivery to the Nucleus," Curr. Drug. Targets, 2: 371-399 (2001).
Kuster, H. et al. Characterization and expression of the gene for the human Fc receptor g subunit. Journal of Biological Chemistry (Apr. 15, 1990), 265(11):6448-6452.
Lanier, L. et al., "Membrane Anchoring of a Human IgG Fc Receptor (CD16) Determined by a Single Amino Acid," Science, 246: 1611-1613 (1989).
Leibson, "Signal transduction during natural killer cell activation: Inside the mind of a killer," Immunity, 6(6):655-661 (1997).
Letter from patentee to EPO for EP Application No. 10791039.0 dated Jul. 15, 2015.
Li, M. et al., "Reconstitution of Human FcgRIII Cell Type Specificity in Transgenic Mice," J Exp Med, 183: 1259-1263 (1996).
Liu, C. et al., "FcgRII on Human B Cells Can Mediate Enhanced Antigen Presentation," Cell Immunol, 167: 188-194 (1996).
Looney, R. et al., "Human monocytes and U937 cells bear two dsitinct Fc receptors for IgG," J Immunol, 135(5): 1641-1647 (1987).
Looney, R. et al., "Identification of a second class of IgG Fc receptors on human neutrophils," Journal of Experimental Medicine, 163:826-836 (1986).

(56) References Cited

OTHER PUBLICATIONS

Louis, E. et al., "Association between polymorphism in IgG Fc receptor IIIA coding gene and biological response to infliximab in Crohn's disease," Alimentary Pharmacology and Therapeutics,19(5):511-519 (2004).
Luo et al., "Synthetic DNA delivery systems," Nature Biotechnol., 18: 33-37 (2000).
Malbec, O. et al., "Negative regulation of hematopoietic cell activation and proliferation by Fc gamma RIIB," Current Topics in Microbiology and Immunology, 244:13-27 (1999).
Masuda, K. et al., "Enhanced binding affinity for FcgRIIIA of fucose-negative antibody is sufficient to induce maximal antibody-dependent cellular cytotoxicity," Molecular Immunology,44:3122-3131 (2007).
Masuda, M et al., "Association of all Three Types of FcgR (CD64, CD32, and CD16) with a g-Chain Homodimer in Cultured Human Monocytes," Journal of Immunology,151(12):7188-7195 (1993).
McKenzie, S. et al., "The Role of the Human Fc Receptor FcgRIIA in the Immune Clearance of Platelets: A Transgenic Mouse Model," Journal of Immunology, 162: 4311-4318 (1999).
McKenzie, S., "Humanized mouse models of FcR clearance in immune platelet disorders," Blood Reviews,16:3-5 (2002).
Meyer T., et al., "Bevacizumab immune complexes activate platelets and induce thrombosis in FCGR2A transgenic mice," J Thrombosis and Haemostasis, 7:-171-181 (2008).
Morgan, A. et al., "Analysis of Fcγ receptor haplotypes in rheumatoid arthritis: FCGR3A remains a major susceptibility gene at this locus, with an additional contribution from FCGR3B," Arthritis Research and Therapy, 8 (1):R5 (2005).
Morgan, A. et al., "Association of FCGR2A and FCGR2A-FCGR3A haplotypes with susceptibility to giant cell arteritis," Arthritis Research and Therapy, 8(4):R109 (2006).
Muller, U., "Ten years of gene targeting: targeted mouse mutants, from vector design to phenotype analysis," Mechanisms of Development, 2:3-21 (1999).
Mullins et al., "Expression of the DBA/2J Ren-2 gene in the adrenal gland of transgenic mice," EMBO, 8: 4065-4072 (1989).
Mullins et al., "Fulminant hypertension in transgenic rats harbouring the mouse Ren-2 gene," Nature, 344: 541-544 (1990).
Nimmerjahn, F. et al., "Divergent Immunoglobulin G Subclass Activity Through Selective Fc Receptor Binding," Science, 310:1510-1512 (2005).
Nimmerjahn, F. et al., "Fc-Receptors as Regulators of Immunity," Advances in Immunology, 96(Ch.5):179-204 (2007).
Nimmerjahn, F. et al., "Fcγ receptors as regulators of immune responses," Nature Reviews, 8:34-47 (2008).
Nimmerjahn, F. et al., "Fcg Receptors: Old Friends and New Family Members," Immunity, 24:19-28 (2006).
Nimmerjahn, F. et al., "FcγRIV: A Novel FcR with Distinct IgG Subclass Specificity," Immunity, 23:41-51 (2005).
Notice of Opposition for EP Application No. 10791039.0 dated Dec. 20, 2018.
Omi, K. et al., "Absence of Association between the Fcg Receptor IIIA-176F/V Polymorphism and the Severity of Malaria in Thai," Japanese Journal of Infectious Disease, 55:167-169 (2002).
Otten, M. et al., "Experimental Antibody Therapy of Liver Metastases Reveals Functional Redundancy between FcgRI and FcgRIV," Journal of Immunology,181:6829-6836 (2008).
Ouma, C. et al., "Association of Fcg receptor IIA (CD32) polymorphism with malarial anemia and high-density parasitemia in infants and young children," American Journal of Tropical Medicine and Hygiene, 74(4):573-577 (2006).
Palu et al., "In pursuit of new developments for gene therapy of human diseases," J. Biotechnol., 68: 1-13 (1999).
Pan, F. et al., "Genetic susceptibility and haplotype analysis between Fcg receptor IIB and IIIA gene with systemic lupus erythematosus in Chinese population," Lupus, 17:733-738 (2008).
Park, S. et al., "Resistance of Fc Receptor-deficient Mice to Fatal Glomerulonephritis," Journal of Clinical Investigation,102(6):1229-1238 (1998).

Partial Search Report issued by the European Patent Office in corresponding Application No. EP 18154933.8, dated Mar. 22, 2018.
Peltz, G. et al., "Cloned and expressed human Fc receptor for IgG mediates anti-CD3-dependent lymphoproliferation," Journal of Immunology,141(6):1891-1896 (1988).
Peltz, G. et al., "Human FcγRIII: Cloning, expression, and identification of the chromosomal locus of two Fc receptors for IgG," PNAS, 86:1013-1017 (1989).
Perussia, B.et al., "Murine natural killer cells express functional Fcg receptor II encoded by the FcgRa gene," Journal of Experimental Medicine, 170:73-86 (1989).
Pfeifer et al., "Gene Therapy: Promises and Problems," Annu. Rev. Genomics. Hum. Genet., 2: 177-211 (2001).
Pietersz et al., "Inhibition of destructive autoimmune arthritis in Fc[gamma] RIIa transgenic mice by small chemical entities," Immun Cell Bio, 87(1): 3-12 (2008).
Raghavan, M. et al., "Fc receptors and their interactions with immunoglobulins," Annual Reviews in Cell Developmental Biology, 12:181-220 (1996).
Rappaport, E. et al., "A soluble form of the human Fc receptor FcgRIIA: cloning, transcript analysis and detection," Experimental Hematology, 21:689-696 (1933).
Ravetch, et al., "Fc receptors," Ann Rev Immunol, 9(1): 457-492 (1991).
Ravetch, et al., "IgG Fc Receptors," Ann Rev Immunol, 19(1): 275-290 (2001).
Ravetch, J. et al., "Alternative membrane forms of FcgRIII(CD16) on human natural killer cells and neutrophils: Cell type-specific expression of two genes that differ in single nucleotide substitutions," Journal of Experimental Medicine, 170:481-497 (1989).
Salmon, J. et al., "Human Receptors for Immunoglobulin G., " Arthritis and Rheumatism,44(4):739-750 (2001).
Scallon, B. et al., "A human immunoglobulin G receptor exists in both polypeptide-anchored and phosphatidylinositol-glycan-anchored forms," PNAS, 86:5079-5083 (1989).
Schmidt, R. et al., "Fc receptors and their interaction with complement in autoimmunity," Immunology Letters,100:56-67 (2005).
Selvaraj, P. et al., "Functional Regulation of Human Neutrophil Fc g Receptors," Immunologic Resarch, 29(1-3):219-229 (2004).
Shoji et al., "Current Status of Delivery Systems to Improve Target Efficacy of Oligonucleotides," Current Pharmaceutical Design, 10: 785-796 (2004).
Siberil, S. et al., "FcgR: The key to optimize therapeutic antibodies?," Critical Reviews in Oncology/Hematology, 62:26-33 (2007).
Simmons, D. et al., "The Fcγ receptor of natural killer cells is a phospholipid-linked membrane protein," Nature, 333:568-570 (1988).
Siriboonrit et al., "Association of Fcgamma Receptor IIB and IIIb Polymorphisms with Susceptibility to Systemic Lupus Erythematosus in Thais," Tissue Antigens, 61(5):2003-2005 (2003).
Smith, P., et al. "Mouse model recapitulating human Fc gamma receptor structural and functional diversity." PNAS USA, 109(16): 6181-6186 (2012).
Sondermann, P. et al., "Crystal structure of the soluble form of the human Fcg-receptor IIb: a new member of the immunoglobulin superfamily at 1.7 a resolution," The EMBO Journal, 18(5):1095-1103 (1999).
Song et al., "Modeling Disease in Human ESCs using an Efficient BAC-Based Homologous Recombination System," Cell Stem Cell, 6:80-89 (2010).
Sparwasser and Eberl, "BAC to Immunology—bacterial artificial chromosome-mediated transgenesis for targeting of immune cells," Immunology, 121:308-313 (2007).
Stacey et al., "Use of Double-Replacement Gene Targeting to Replace the Murine α-Lactalbumin Gene with its Human Counterpart in embryonic Stem Cells and Mice," Molecular and Cellular Biology, 14(2):1009-1016 (1994).
Stavenhagen et al., "Fc Optimization of Therapeutic Antibodies Enhances Their Ability to Kill Tumor Cells in vitro and Controls Tumor Expansion in vivo via Low-Affinity activating fc gamma receptors," AACR, 67(18): 8882-8890 (2007).

(56) References Cited

OTHER PUBLICATIONS

Stuart, S. et al., "Isolation and expression of cDNA clones encoding a human receptor for IgG (FcgRII)," Journal of Experimental Medicine, 166:1668-1684 (1987).
Su, K. et al., "Genomic organization of classical human low-affinity Fcg receptor genes," Genes and Immunity, 3(Suppl 1):S51-S56 (2002).
Sullivan et al., "Targeted Replacement of the Mouse Apolipoprotein E Gene with the Common Human APOE3 Allele Enhances Dier-Induced Hypercholesterolemia and Atherosclerosis," J Biol Chem, 272(29):17971-17980 (1997).
Takai, T. et al., "Augmented humoral and anaphylactic responses in FcgRII-deficient mice," Nature, 379:346-349 (1996).
Takai, T. et al., "FcR γ Chain Deletion Results in Pleiotrophic Effector Cell Defects," Cell, 76:519-529 (1994).
Takai, T., "Fc Receptors and Their Role in Immune Regulation and Autoimmunity," Journal of Clinical Immunology, 25(1):1-18 (2005).
Takai, T., "Roles of Fc Receptors in Autoimmunity," Nature Reviews, 2:580-592 (2002).
Taurog et al., "Cell Surface Expression and Recognition as an Alloantigen in the Absence of Human B2-Microglobulin," J. Immunol., 141(11): 4020-4023 (1988).
Trounstine, M. et al., "Reactivity of cloned, expressed human FcgRII isoforms with monoclonal antibodies which distinguish cell-type-specific and allelic forms of FcgRII," International Immunology, 2(4):303-310 (1990).
Tsuchiya, N. et al., "Role of Fcγ receptor IIb polymorphism in the genetic background of systemic lupus eryhematosus: Insights from Asia," Autoimmunity, 38(5):347-352 (2005).
Tsukahara S., et al., "A polymorphism in the gene encoding the Fcgamma IIIA receptor is a possible genetic marker to predict the primary response to infliximab in Japanese patients with rheumatoid arthritis." Ann Rheum Dis., 67 (12):1791-1792 (2008).
Tuijnam, WB et al., "Human Low-Affinity IgG Receptor FcgRIIa (CD32) Introduced Into Mouse Fibroblasts Mediates Phagocytosis of Sensitized Erythrocytes," Blood, 79(7):1651-1656 (1992).
Valenzuela et al., "High-throughput engineering of the mouse genome coupled with high-resolution expression analysis," Nature Biotech, 21:652-659 (2003).
Van De Winkel, J. et al., "Biological functioning of human IgG Fc receptors," Research in Immunology, 141(1):64-67 (1990).
Van De Winkel, J. et al., "Biology of Human Immunoglobulin G Fc Receptors," Journal of Leukocyte Biology, 49:511-524 (1991).
Van De Winkel, J. et al., "Human IgG Fc receptor heterogeneity: molecular aspects and clinical implications," Immunology Today, 14(5):215-221 (1993).
Van Den Herik-Oudijk, I. et al., "Functional Differences Between Two Fc Receptor ITAM Signaling Motifs," Blood, 86(9):3302-3307 (1995).
Van Egmond et al., "Human Immunoglobulin a Receptor (FCαRI, CD89) Function in Transgenic Mice Requires Both FcR 'Y' Chain and CR3 (CD11b/CD18)," Blood, 93:4387-4394 (1999).
Vanvugt, M. et al., "FcR g-Chain is Essential for Both Surface Expression and Function of Human FcgRI (CD64) In Vivo," Blood, 87(9):3593-3599 (1996).
Verbeek, J. et al., "The role of FcR in immunity: lessons from gene targeting in mice," Research in Immunology,147(7):466-474 (1997).
Verma et al., "Gene therapy—promises, problems and prospects," Nature, 389: 239-242 (1997).
Wall, "Transgenic Livestock: Progress and Prospects for the Future," Theriogenology, 45: 57-68 (1996).
Warmerdam, P. et al., "A single amino acid in the second Ig-like domain of the human Fcg receptor II is critical for human IgG2 binding," Journal of Immunology,147(4):1338-1343 (1991).
Warmerdam, P. et al., "Interaction of a human FcgRIIb1 (CD32) isoform with murine and human IgG subclasses," International Immunology, 5(3):239-247 (1993).
Weinshank, R. et al., "Function and regulation of a murine macrophage-specific IgG Fc receptor, FcgR-a," Journal of Experimental Medicine, 167:1909-1925 (1988).
Written opinion of the International Searching Authority for PCT application No. PCT/US2010/060925, dated Mar. 14, 2011.
Yu et al., "Coordinate Regulation of RAG1 and RAG2 by Cell Type-Specific DNA Elements 5' of RAG2," Science, 285:1080-1084 (1999).
Zuniga, R. et al., Low-Binding Alleles of Fcg Receptor Types IIA and IIIA are Inherited Independently and are Associated With Systemic Lupus Erythematosus in Hispanic Patients, Arthritis and Rheumatism, 44 (2):361-367 (2001).

* cited by examiner

```
                       SEQUENCE LISTING

<160> NUMBER OF SEQ ID NOS: 38

<210> SEQ ID NO 1
<211> LENGTH: 21
<212> TYPE: DNA
<213> ORGANISM: Artificial Sequence
<220> FEATURE:
<223> OTHER INFORMATION: synthetic

<400> SEQUENCE: 1
accaggatat gacctgtaga g                                              21

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
gtccatgggt aagtagaaac a                                              21

<210> SEQ ID NO 3
<211> LENGTH: 65
<212> TYPE: DNA
<213> ORGANISM: Artificial Sequence
<220> FEATURE:
<223> OTHER INFORMATION: synthetic

<400> SEQUENCE: 3
atgcgagctc atgcatctat gtcgggtgcg gagaaagagg taatgcattc ttgcccaata    60
cttac                                                                65

<210> SEQ ID NO 4
<211> LENGTH: 21
<212> TYPE: DNA
<213> ORGANISM: Artificial Sequence
<220> FEATURE:
<223> OTHER INFORMATION: synthetic

<400> SEQUENCE: 4
```
actcatggag cctcaacagg a            21

<210> SEQ ID NO 5
<211> LENGTH: 23
<212> TYPE: DNA
<213> ORGANISM: Artificial Sequence
<220> FEATURE:
<223> OTHER INFORMATION: synthetic

<400> SEQUENCE: 5
atcctgagta tactatgaca aga           23

<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6
actagtgaga cgtgctactt c            21

<210> SEQ ID NO 7
<211> LENGTH: 21
<212> TYPE: DNA
<213> ORGANISM: Artificial Sequence
<220> FEATURE:
<223> OTHER INFORMATION: synthetic

<400> SEQUENCE: 7
ctcccactca tgatctatag a            21

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
tggagcctca acaggactcc a            21

<210> SEQ ID NO 9
<211> LENGTH: 42
<212> TYPE: DNA
<213> ORGANISM: Artificial Sequence
<220> FEATURE:
<223> OTHER INFORMATION: synthetic

<400> SEQUENCE: 9
gtccatgggt aagtagaaac attcgctacc ttaggaccgt ta            42

<210> SEQ ID NO 10
<211> LENGTH: 42
<212> TYPE: DNA
<213> ORGANISM: Artificial Sequence
<220> FEATURE:
<223> OTHER INFORMATION: synthetic

<400> SEQUENCE: 10
cgggtgcgga gaaagaggta atgcattctt gcccaatact ta            42

<210> SEQ ID NO 11
<211> LENGTH: 22
<212> TYPE: DNA
<213> ORGANISM: Artificial Sequence
<220> FEATURE:
<223> OTHER INFORMATION: synthetic

<400> SEQUENCE: 11
gccagccaca aaggagataa tc                                        22

<210> SEQ ID NO 12
<211> LENGTH: 22
<212> TYPE: DNA
<213> ORGANISM: Artificial Sequence
<220> FEATURE:
<223> OTHER INFORMATION: synthetic

<400> SEQUENCE: 12
gcaacattta ggacaactcg gg                                        22

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
gatttcctaa ccacctaccc c                                         21

<210> SEQ ID NO 14
<211> LENGTH: 19
<212> TYPE: DNA
<213> ORGANISM: Artificial Sequence
<220> FEATURE:
<223> OTHER INFORMATION: synthetic

<400> SEQUENCE: 14
tcttttccaa tggcagttg                                            19

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
cccaggtaag tcgtgatgaa acag                                      24

<210> SEQ ID NO 16
<211> LENGTH: 21
<212> TYPE: DNA
<213> ORGANISM: Artificial Sequence
<220> FEATURE:
<223> OTHER INFORMATION: synthetic

<400> SEQUENCE: 16
ctcccactca tgatctatag a                                         21

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
tggagcctca acaggactcc a                                         21

<210> SEQ ID NO 18
<211> LENGTH: 21
<212> TYPE: DNA
<213> ORGANISM: Artificial Sequence
<220> FEATURE:
<223> OTHER INFORMATION: synthetic

<400> SEQUENCE: 18
cacacatctc ctggtgactt g                                              21

<210> SEQ ID NO 19
<211> LENGTH: 42
<212> TYPE: DNA
<213> ORGANISM: Artificial Sequence
<220> FEATURE:
<223> OTHER INFORMATION: synthetic

<400> SEQUENCE: 19
caactgccat tggaaaagac tcgagtgcca tttcattacc tc                       42

<210> SEQ ID NO 20
<211> LENGTH: 42
<212> TYPE: DNA
<213> ORGANISM: Artificial Sequence
<220> FEATURE:
<223> OTHER INFORMATION: synthetic

<400> SEQUENCE: 20
taaacccgcg gtggagctcg ccagccacaa aggagataat ca                       42

<210> SEQ ID NO 21
<211> LENGTH: 42
<212> TYPE: DNA
<213> ORGANISM: Artificial Sequence
<220> FEATURE:
<223> OTHER INFORMATION: synthetic

<400> SEQUENCE: 21
ccatgggtaa gtagaaactc tagaccccg ggctcgataa ct                        42

<210> SEQ ID NO 22
<211> LENGTH: 21
<212> TYPE: DNA
<213> ORGANISM: Artificial Sequence
<220> FEATURE:
<223> OTHER INFORMATION: synthetic

<400> SEQUENCE: 22
accaggatat gacctgtaga g                                              21

<210> SEQ ID NO 23
<211> LENGTH: 20
<212> TYPE: DNA
<213> ORGANISM: Artificial Sequence
<220> FEATURE:
<223> OTHER INFORMATION: synthetic

<400> SEQUENCE: 23
gtttctactt acccatggac                                                20

<210> SEQ ID NO 24
<211> LENGTH: 22
<212> TYPE: DNA
<213> ORGANISM: Artificial Sequence
<220> FEATURE:
<223> OTHER INFORMATION: synthetic

```
<400> SEQUENCE: 24
aaatacacac tgccacagac ag                                          22

<210> SEQ ID NO 25
<211> LENGTH: 22
<212> TYPE: DNA
<213> ORGANISM: Artificial Sequence
<220> FEATURE:
<223> OTHER INFORMATION: synthetic

<400> SEQUENCE: 25
cctcttttgt gagtttcctg tg                                          22

<210> SEQ ID NO 26
<211> LENGTH: 23
<212> TYPE: DNA
<213> ORGANISM: Artificial Sequence
<220> FEATURE:
<223> OTHER INFORMATION: synthetic

<400> SEQUENCE: 26
gagtatacta tgacaagagc atc                                         23

<210> SEQ ID NO 27
<211> LENGTH: 21
<212> TYPE: DNA
<213> ORGANISM: Artificial Sequence
<220> FEATURE:
<223> OTHER INFORMATION: synthetic

<400> SEQUENCE: 27
actagtgaga cgtgctactt c                                           21

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
ctcccactca tgatctatag a                                           21

<210> SEQ ID NO 29
<211> LENGTH: 22
<212> TYPE: DNA
<213> ORGANISM: Artificial Sequence
<220> FEATURE:
<223> OTHER INFORMATION: synthetic

<400> SEQUENCE: 29 cttttttatgg tcccacaatc ag                                         22

<210> SEQ ID NO 30
<211> LENGTH: 42
<212> TYPE: DNA
<213> ORGANISM: Artificial Sequence
<220> FEATURE:
<223> OTHER INFORMATION: synthetic

<400> SEQUENCE: 30
gtccatgggt aagtagaaac attcgctacc ttaggaccgt ta                    42

<210> SEQ ID NO 31
```

-continued

```
<211> LENGTH: 42
<212> TYPE: DNA
<213> ORGANISM: Artificial Sequence
<220> FEATURE:
<223> OTHER INFORMATION: synthetic

<400> SEQUENCE: 31
gcttatcgat accgtcgaca aatacacact gccacagaca gg                         42

<210> SEQ ID NO 32
<211> LENGTH: 317
<212> TYPE: PRT
<213> ORGANISM: Artificial Sequence
<220> FEATURE:
<223> OTHER INFORMATION: synthetic

<400> SEQUENCE: 32

Met Thr Met Glu Thr Gln Met Ser Gln Asn Val Cys Pro Arg Asn Leu
1               5                   10                  15

Trp Leu Gln Pro Leu Thr Val Leu Leu Leu Leu Ala Ser Ala Asp
            20                  25                  30

Ser Gln Ala Ala Ala Pro Pro Lys Ala Val Leu Lys Leu Glu Pro Pro
        35                  40                  45

Trp Ile Asn Val Leu Gln Glu Asp Ser Val Thr Leu Thr Cys Gln Gly
    50                  55                  60

Ala Arg Ser Pro Glu Ser Asp Ser Ile Gln Trp Phe His Asn Gly Asn
65                  70                  75                  80

Leu Ile Pro Thr His Thr Gln Pro Ser Tyr Arg Phe Lys Ala Asn Asn
                85                  90                  95

Asn Asp Ser Gly Glu Tyr Thr Cys Gln Thr Gly Gln Thr Ser Leu Ser
            100                 105                 110

Asp Pro Val His Leu Thr Val Leu Ser Glu Trp Leu Val Leu Gln Thr
        115                 120                 125

Pro His Leu Glu Phe Gln Glu Gly Glu Thr Ile Met Leu Arg Cys His
    130                 135                 140

Ser Trp Lys Asp Lys Pro Leu Val Lys Val Thr Phe Phe Gln Asn Gly
145                 150                 155                 160

Lys Ser Gln Lys Phe Ser His Leu Asp Pro Thr Phe Ser Ile Pro Gln
                165                 170                 175

Ala Asn His Ser His Ser Gly Asp Tyr His Cys Thr Gly Asn Ile Gly
            180                 185                 190

Tyr Thr Leu Phe Ser Ser Lys Pro Val Thr Ile Thr Val Gln Val Pro
        195                 200                 205

Ser Met Gly Ser Ser Ser Pro Met Gly Ile Ile Val Ala Val Val Ile
    210                 215                 220

Ala Thr Ala Val Ala Ala Ile Val Ala Ala Val Ala Leu Ile Tyr
225                 230                 235                 240

Cys Arg Lys Lys Arg Ile Ser Ala Asn Ser Thr Asp Pro Val Lys Ala
                245                 250                 255

Ala Gln Phe Glu Pro Pro Gly Arg Gln Met Ile Ala Ile Arg Lys Arg
            260                 265                 270

Gln Leu Glu Glu Thr Asn Asn Asp Tyr Glu Thr Ala Asp Gly Gly Tyr
        275                 280                 285

Met Thr Leu Asn Pro Arg Ala Pro Thr Asp Asp Lys Asn Ile Tyr
    290                 295                 300

Leu Thr Leu Pro Pro Asn Asp His Val Asn Ser Asn Asn
305                 310                 315
```

<210> SEQ ID NO 33
<211> LENGTH: 303
<212> TYPE: PRT
<213> ORGANISM: Artificial Sequence
<220> FEATURE:
<223> OTHER INFORMATION: synthetic

<400> SEQUENCE: 33

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Ala Pro Lys Ala Val Leu Lys Leu Glu
        35                  40                  45

Pro Gln Trp Ile Asn Val Leu Gln Glu Asp Ser Val Thr Leu Thr Cys
    50                  55                  60

Arg Gly Thr His Ser Pro Glu Ser Asp Ser Ile Gln Trp Phe His Asn
65                  70                  75                  80

Gly Asn Leu Ile Pro Thr His Thr Gln Pro Ser Tyr Arg Phe Lys Ala
                85                  90                  95

Asn Asn Asn Asp Ser Gly Glu Tyr Thr Cys Gln Thr Gly Gln Thr Ser
            100                 105                 110

Leu Ser Asp Pro Val His Leu Thr Val Leu Ser Glu Trp Leu Val Leu
        115                 120                 125

Gln Thr Pro His Leu Glu Phe Gln Glu Gly Glu Thr Ile Val Leu Arg
    130                 135                 140

Cys His Ser Trp Lys Asp Lys Pro Leu Val Lys Val Thr Phe Phe Gln
145                 150                 155                 160

Asn Gly Lys Ser Lys Lys Phe Ser Arg Ser Asp Pro Asn Phe Ser Ile
                165                 170                 175

Pro Gln Ala Asn His Ser His Ser Gly Asp Tyr His Cys Thr Gly Asn
            180                 185                 190

Ile Gly Tyr Thr Leu Tyr Ser Ser Lys Pro Val Thr Ile Thr Val Gln
        195                 200                 205

Ala Pro Ser Ser Ser Pro Met Gly Ile Ile Val Ala Val Val Thr Gly
    210                 215                 220

Ile Ala Val Ala Ala Ile Val Ala Ala Val Ala Leu Ile Tyr Cys
225                 230                 235                 240

Arg Lys Lys Arg Ile Ser Ala Leu Pro Gly Tyr Pro Glu Cys Arg Glu
                245                 250                 255

Met Gly Glu Thr Leu Pro Glu Lys Pro Ala Asn Pro Thr Asn Pro Asp
            260                 265                 270

Glu Ala Asp Lys Val Gly Ala Glu Asn Thr Ile Thr Tyr Ser Leu Leu
        275                 280                 285

Met His Pro Asp Ala Leu Glu Glu Pro Asp Asp Gln Asn Arg Ile
    290                 295                 300
```

<210> SEQ ID NO 34
<211> LENGTH: 323
<212> TYPE: PRT
<213> ORGANISM: Artificial Sequence
<220> FEATURE:
<223> OTHER INFORMATION: synthetic

<400> SEQUENCE: 34

```
Met Gly Ile Leu Ser Phe Leu Pro Val Leu Ala Thr Glu Ser Asp Trp
```

```
1               5                   10                  15
Ala Asp Cys Lys Ser Pro Gln Pro Trp Gly His Met Leu Leu Trp Thr
                20                  25                  30
Ala Val Leu Phe Leu Ala Pro Val Ala Gly Thr Pro Ala Ala Pro Pro
                35                  40                  45
Lys Ala Val Leu Lys Leu Glu Pro Gln Trp Ile Asn Val Leu Gln Glu
                50                  55                  60
Asp Ser Val Thr Leu Thr Cys Arg Gly Thr His Ser Pro Glu Ser Asp
65                  70                  75                  80
Ser Ile Pro Trp Phe His Asn Gly Asn Leu Ile Pro Thr His Thr Gln
                    85                  90                  95
Pro Ser Tyr Arg Phe Lys Ala Asn Asn Asn Asp Ser Gly Glu Tyr Thr
                100                 105                 110
Cys Gln Thr Gly Gln Thr Ser Leu Ser Asp Pro Val His Leu Thr Val
                115                 120                 125
Leu Ser Glu Trp Leu Val Leu Gln Thr Pro His Leu Glu Phe Gln Glu
130                 135                 140
Gly Glu Thr Ile Val Leu Arg Cys His Ser Trp Lys Asp Lys Pro Leu
145                 150                 155                 160
Val Lys Val Thr Phe Phe Gln Asn Gly Lys Ser Lys Lys Phe Ser Arg
                    165                 170                 175
Ser Asp Pro Asn Phe Ser Ile Pro Gln Ala Asn His Ser His Ser Gly
                180                 185                 190
Asp Tyr His Cys Thr Gly Asn Ile Gly Tyr Thr Leu Tyr Ser Ser Lys
                195                 200                 205
Pro Val Thr Ile Thr Val Gln Ala Pro Ser Ser Ser Pro Met Gly Ile
                210                 215                 220
Ile Val Ala Val Val Thr Gly Ile Ala Val Ala Ala Ile Val Ala Ala
225                 230                 235                 240
Val Val Ala Leu Ile Tyr Cys Arg Lys Lys Arg Ile Ser Ala Asn Ser
                    245                 250                 255
Thr Asp Pro Val Lys Ala Ala Gln Phe Glu Pro Pro Gly Arg Gln Met
                260                 265                 270
Ile Ala Ile Arg Lys Arg Gln Pro Glu Glu Thr Asn Asn Asp Tyr Glu
                275                 280                 285
Thr Ala Asp Gly Gly Tyr Met Thr Leu Asn Pro Arg Ala Pro Thr Asp
                290                 295                 300
Asp Asp Lys Asn Ile Tyr Leu Thr Leu Pro Pro Asn Asp His Val Asn
305                 310                 315                 320
Ser Asn Asn

<210> SEQ ID NO 35
<211> LENGTH: 290
<212> TYPE: PRT
<213> ORGANISM: Artificial Sequence
<220> FEATURE:
<223> OTHER INFORMATION: synthetic

<400> SEQUENCE: 35

Met Gly Gly Gly Ala Gly Glu Arg Leu Phe Thr Ser Ser Cys Leu Val
1               5                   10                  15
Gly Leu Val Pro Leu Gly Leu Arg Ile Ser Leu Val Thr Cys Pro Leu
                20                  25                  30
Gln Cys Gly Ile Met Trp Gln Leu Leu Leu Pro Thr Ala Leu Leu Leu
                35                  40                  45
```

```
Leu Val Ser Ala Gly Met Arg Thr Glu Asp Leu Pro Lys Ala Val Val
 50                  55                  60

Phe Leu Glu Pro Gln Trp Tyr Arg Val Leu Glu Lys Asp Ser Val Thr
 65                  70                  75                  80

Leu Lys Cys Gln Gly Ala Tyr Ser Pro Glu Asp Asn Ser Thr Gln Trp
                 85                  90                  95

Phe His Asn Glu Ser Leu Ile Ser Ser Gln Ala Ser Ser Tyr Phe Ile
                100                 105                 110

Asp Ala Ala Thr Val Asp Asp Ser Gly Glu Tyr Arg Cys Gln Thr Asn
                115                 120                 125

Leu Ser Thr Leu Ser Asp Pro Val Gln Leu Glu Val His Ile Gly Trp
                130                 135                 140

Leu Leu Leu Gln Ala Pro Arg Trp Val Phe Lys Glu Glu Asp Pro Ile
145                 150                 155                 160

His Leu Arg Cys His Ser Trp Lys Asn Thr Ala Leu His Lys Val Thr
                165                 170                 175

Tyr Leu Gln Asn Gly Lys Gly Arg Lys Tyr Phe His His Asn Ser Asp
                180                 185                 190

Phe Tyr Ile Pro Lys Ala Thr Leu Lys Asp Ser Gly Ser Tyr Phe Cys
                195                 200                 205

Arg Gly Leu Phe Gly Ser Lys Asn Val Ser Ser Glu Thr Val Asn Ile
                210                 215                 220

Thr Ile Thr Gln Gly Leu Ala Val Ser Thr Ile Ser Ser Phe Phe Pro
225                 230                 235                 240

Pro Gly Tyr Gln Val Ser Phe Cys Leu Val Met Val Leu Leu Phe Ala
                245                 250                 255

Val Asp Thr Gly Leu Tyr Phe Ser Val Lys Thr Asn Ile Arg Ser Ser
                260                 265                 270

Thr Arg Asp Trp Lys Asp His Lys Phe Lys Trp Arg Lys Asp Pro Gln
                275                 280                 285

Asp Lys
    290

<210> SEQ ID NO 36
<211> LENGTH: 233
<212> TYPE: PRT
<213> ORGANISM: Artificial Sequence
<220> FEATURE:
<223> OTHER INFORMATION: synthetic

<400> SEQUENCE: 36

Met Trp Gln Leu Leu Leu Pro Thr Ala Leu Leu Leu Leu Val Ser Ala
  1               5                  10                  15

Gly Met Arg Thr Glu Asp Leu Pro Lys Ala Val Val Phe Leu Glu Pro
                 20                  25                  30

Gln Trp Tyr Ser Val Leu Glu Lys Asp Ser Val Thr Leu Lys Cys Gln
                 35                  40                  45

Gly Ala Tyr Ser Pro Glu Asp Asn Ser Thr Gln Trp Phe His Asn Glu
 50                  55                  60

Asn Leu Ile Ser Ser Gln Ala Ser Ser Tyr Phe Ile Asp Ala Ala Thr
 65                  70                  75                  80

Val Asn Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
                100                 105                 110
```

```
Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
        210                 215                 220

Leu Tyr Phe Ser Val Lys Thr Asn Ile
225                 230

<210> SEQ ID NO 37
<211> LENGTH: 40
<212> TYPE: DNA
<213> ORGANISM: Artificial Sequence
<220> FEATURE:
<223> OTHER INFORMATION: synthetic

<400> SEQUENCE: 37
atcggggata gagatgtttg ccgcgatcgc ggtaccgggc                           40

<210> SEQ ID NO 38
<211> LENGTH: 40
<212> TYPE: DNA
<213> ORGANISM: Artificial Sequence
<220> FEATURE:
<223> OTHER INFORMATION: synthetic

<400> SEQUENCE: 38
ttatacgaag ttataccggt gcattcttgc ccaatactta                           40
```

HUMANIZED LOW AFFINITY FCγR MOUSE CELLS

CROSS-REFERENCE TO RELATED APPLICATIONS

This application is a continuation of U.S. Ser. No. 15/601,363, filed May 22, 2017, which is a continuation of U.S. Ser. No. 14/800,253, filed Jul. 15, 2015, currently issued as U.S. Pat. No. 9,687,566, which is a continuation of U.S. Ser. No. 14/152,106, filed Jan. 10, 2014, currently issued as U.S. Pat. No. 9,089,599, which is a divisional of U.S. Ser. No. 13/466,225, filed on May 8, 2012, currently issued as U.S. Pat. No. 8,658,853, which is a continuation of Ser. No. 12/971,080, filed on Dec. 17, 2010, currently issued as U.S. Pat. No. 8,658,154, which claims the benefit of the filing date under 35 USC § 119(e), and is a nonprovisional, of U.S. Provisional Patent Application Ser. No. 61/288,562, filed Dec. 21, 2009, which applications are hereby incorporated by reference.

FIELD OF INVENTION

The field of invention is genetically modified non-human animals that lack endogenous murine FcγR genes, including genetically modified animals that comprise a replacement of endogenous FcγR genes with human FcγR genes, and including mice that are capable of expressing at least two, three, four, or five functional human low affinity FcγR genes, and including genetically modified mice comprising immune cells that do not express endogenous low affinity FcγR genes.

BACKGROUND

Fc receptors (FcRs) are proteins found on the surface of cells of the immune system that carry out a variety of functions of the immune system in mammals. FcRs exist in a variety of types, on a variety of cells, and mediate a variety of immune functions such as, for example, binding to antibodies that are attached to infected cells or invading pathogens, stimulating phagocytic or cytotoxic cells to destroy microbes, or infected cells by antibody-mediated phagocytosis or antibody-dependent cell-mediated cytotoxicity (ADCC).

ADCC is a process whereby effector cells of the immune system lyse a target cell bound by antibodies. This process depends on prior exposure to a foreign antigen or cell, resulting in an antibody response. ADCC can be mediated through effector cells such as, for example, natural killer (NK) cells, by binding of FcR expressed on the surface of the effector cell to the Fc portion of the antibody which itself is bound to the foreign antigen or cell. Because of the central role that FcRs play in the immune response, useful non-human animals that co-express multiple human FcRs are needed, including non-human animals that co-express multiple human low affinity FcRs. There exists a need for non-human animal models of human FcR function and human processes of ADCC for the study and elucidation of human disease therapies, in particular anti-tumor therapies and therapies for treating autoimmune diseases, and pharmaceutical drug development, in particular in the development, design, and testing of human antibody pharmaceuticals.

SUMMARY

Figure 1:
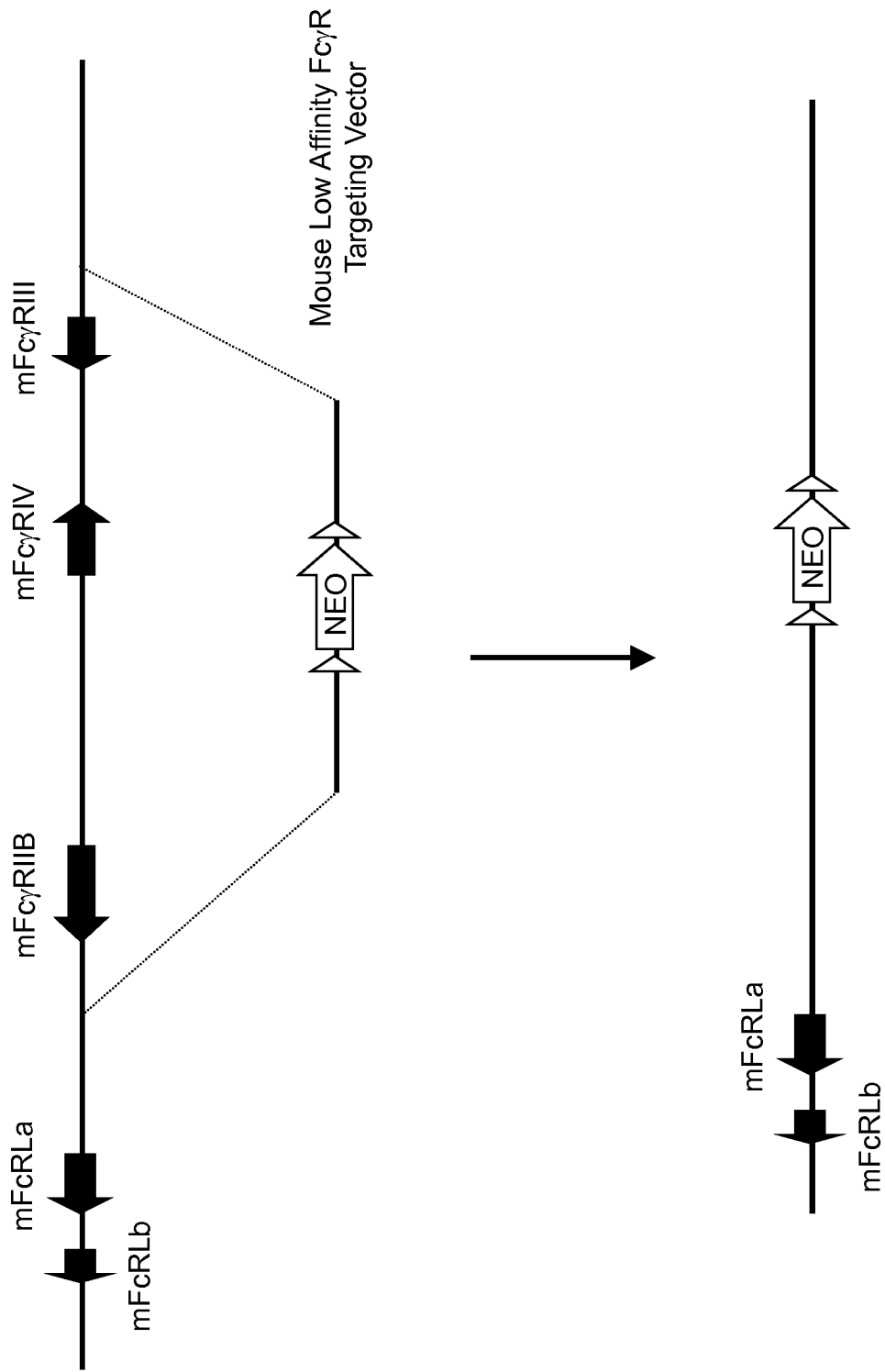
FIG. 1 is a schematic depiction of a wild type low affinity FcγR locus in a mouse, showing mouse FcγRIIB, FcγRIV and FcγRIII genes and a mouse FcγR targeting vector used for a targeted deletion of these genes, which includes a neomycin cassette flanked by site-specific recombination sites.

Genetically modified cells, non-human embryos, non-human animals and methods and compositions for making and using them are provided. In various aspects, the non-human animals comprise a human FcγR receptor, a deletion of an endogenous low affinity FcγR receptor, and/or a replacement of an endogenous FcγR receptor with a human FcγR receptor at an endogenous mouse low affinity FcγR locus.

In one aspect, genetically modified cells, non-human embryos, and non-human animals are provided that comprise a functional FcR γ-chain, wherein the cells, embryos, and animals comprise a further modification comprising a replacement of the low affinity endogenous non-human FcγR gene sequences (e.g., FcγRIIB, FcγRIV and FcγRIII) with one or more low affinity human FcγR gene sequences (e.g., selected from FcγRIIA, FcγRIIB, FcγRIIC, FcγRIIIA, FcγRIIIB, and a combination thereof).

In one embodiment, the cells, non-human embryos, and non-human animals are murine. In one embodiment, the functional FcR γ-chain is a mouse FcR γ-chain. In one embodiment, the mouse FcR γ-chain is an FcR γ-chain endogenous to the mouse, the cell, or the embryo.

In one embodiment, the cells, embryos, and animals are mice, and the mice express a functional α-chain of a human low affinity FcγR receptor and a functional endogenous mouse γ-chain.

In one aspect, a genetically modified mouse is provided, wherein the mouse does not express an endogenous α-chain selected from an FcγRIIB α-chain, an FcγRIV α-chain, an FcγRIII α-chain, and a combination thereof; wherein the mouse expresses a functional endogenous mouse γ-chain.

In a specific embodiment, the mouse does not express a functional FcγRIIB α-chain, does not express a functional FcγRIV α-chain, and does not express a functional FcγRIII α-chain.

In one embodiment, the mouse genome comprises a deletion of an endogenous FcγRIIB α-chain, a deletion of an endogenous FcγRIV α-chain, and a deletion of an endogenous FcγRIII α-chain.

In one embodiment, the mouse comprises a deletion of an endogenous FcγRIIB α-chain, a deletion of an endogenous FcγRIV α-chain, and a deletion of an endogenous FcγRIII α-chain, and further comprises a reduced ability to make an immune response to an antigen as compared with a wild type mouse's ability with respect to the same antigen. In one embodiment, the reduced immune response includes a decreased antibody-dependent cell-mediated cytotoxicity (ADCC). In one embodiment, the reduced immune response includes a reduced ability in a cell killing assay to achieve antibody-dependent NK cell killing. In specific embodiments, the reduction in ADCC or antibody-dependent NK cell killing is at least 50%, in one embodiment at least 75%, in one embodiment at least 90%.

In one embodiment, the mouse comprises a deletion of an endogenous FcγRIIB α-chain, a deletion of an endogenous FcγRIV α-chain, and a deletion of an endogenous FcγRIII α-chain, and further comprises an increased humoral antibody response upon immunization with an antigen as compared to a wild type mouse, e.g., a mouse of the same or similar strain that does not comprise the deletion. In one embodiment, the increased humoral antibody response is 2-fold as compared to a wild type mouse. In one embodiment, the increased humoral antibody response is 3-fold as compared to a wild type mouse. In one embodiment, the increased humoral antibody response is 5-fold as compared to a wild type mouse. In one embodiment, the increased humoral antibody response is 7-fold as compared to a wild type mouse. In one embodiment, the increased humoral antibody response is 10-fold as compared to a wild type mouse. In a specific embodiment, humoral antibody response is measured by micrograms of antibody that specifically binds an antigen (with which the mouse has been immunized) per microgram of serum protein from the mouse. In one embodiment, the increased humoral antibody response is with respect to an antigen to which a wild type mouse exhibits tolerance, or to an antigen which in a wild type mouse exhibits a poor or minimal humoral immune response. In a specific embodiment, the antigen is a mouse antigen. In a specific embodiment, the antigen is a human antigen that exhibits an identity with a mouse protein of at least about 95%, 96%, 97%, 98%, or 99%.

In one aspect, a genetically modified mouse is provided, comprising a replacement of a low affinity mouse FcγR α-chain gene with a low affinity human FcγR α-chain gene, wherein the replacement is at the endogenous mouse FcγR α-chain gene locus. In one embodiment, the low affinity mouse FcγR α-chain gene is selected from an FcγRIIB, FcγRIV and an FcγRIII α-chain gene. In a specific embodiment, a genetically modified mouse is provided, wherein the mouse expresses an endogenous FcR γ-chain, and wherein the low affinity human FcγR α-chain gene is FcγRIIIA α-chain. In another specific embodiment, the genetically modified mouse expresses an endogenous FcR γ-chain and a functional human FcγRIIIA α-chain on NK cells. In a specific embodiment, the functionality of FcγRIIIA α-chain on NK cells is reflected by human antibody-mediated NK killing (e.g., ADCC mediated by a human antibody).

In one aspect, a genetically modified cell, non-human embryo, or non-human animal is provided, wherein the genetic modification comprises a replacement of at least one endogenous low affinity FcγR α-chain gene with a human FcγR α-chain gene, and the cell, embryo, or animal expresses a functional FcR γ-chain. In one embodiment, the functional FcRγ-chain is an endogenous FcR γ-chain. In one embodiment, the low affinity human FcγR α-chain gene is selected from an FcγRIIA α-chain gene, an FcγRIIIA α-chain gene, and a combination thereof. In a specific embodiment, the human FcγRIIA gene comprises a polymorphism, wherein the polymorphism is selected from a 131His low responder polymorphism and a 131Arg high responder polymorphism. In a specific embodiment, the FcγRIIA polymorphism is the 131His low responder polymorphism. In one embodiment, the FcγRIIIA gene is a specific allelic variant, wherein the allelic variant is selected from a 158Val variant and a 158Phe variant. In a specific embodiment, the FcγRIIIA allelic variant is the 158Val variant.

In one embodiment the low affinity human FcγR gene is selected from an FcγRIIB, FcγRIIC, an FcγRIIIB gene, and a combination thereof. In a specific embodiment, the human FcγRIIB gene comprises an amino acid substitution, wherein the substitution is selected from an 232Ile or a 232Thr substitution. In another specific embodiment, amino acid substitution is a 232Ile substitution. In a specific embodiment, the FcγRIIIB gene is a specific allelic variant, wherein the allelic variant is selected from a NA1 variant and a NA2 variant. In another specific embodiment, the FcγRIIIB allelic variant is a NA2 variant.

In one embodiment the low-affinity human FcγR α-chain gene is selected from a FcγRIIA, FcγRIIB, FcγRIIC, FcγRIIIA, FcγRIIIB α-chain gene, and a combination thereof.

In one embodiment, the low affinity mouse FcγRIV α-chain gene and the FcγRIII α-chain gene are replaced with at least one low affinity human FcγR α-chain gene. In one embodiment, the low affinity mouse FcγRIV α-chain gene and the FcγRIIB α-chain gene are replaced with at least one low affinity human FcγR α-chain gene. In one embodiment, the low affinity mouse FcγRIIB α-chain gene and the FcγRIII α-chain gene are replaced with at least one low affinity human FcγR α-chain gene. In a specific embodiment, the at least one low affinity human FcγR α-chain gene is selected from an FcγRIIA, FcγRIIB, FcγRIIC, FcγRIIIA, FcγRIIIB α-chain gene, and a combination thereof. In another specific embodiment, the at least one low affinity human FcγR α-chain gene is selected from an FcγRIIA α-chain gene, an FcγRIIIA α-chain gene, and a combination thereof. In another specific embodiment, the at least one low affinity human FcγR α-chain gene is selected from an FcγRIIB, FcγRIIC, FcγRIIIB α-chain gene, and a combination thereof. In another specific embodiment, the low affinity mouse FcγR genes are replaced with a human FcγRIIA α-chain gene and a human FcγRIIIA α-chain gene. In another specific embodiment, the low affinity human FcγRIIA and FcγRIIIA α-chain genes comprise variants, wherein the FcγRIIA α-chain gene comprises a 131His variant and the FcγRIIIA α-chain gene comprises a 158Val variant. In another specific embodiment, the low affinity mouse FcγR α-chain genes are replaced with the following low affinity human FcγR α-chain genes: FcγRIIB, FcγRIIC and FcγRIIIB. In another specific embodiment, the low affinity human FcγRIIB α-chain gene and FcγRIIIB α-chain gene comprise variants, wherein the FcγRIIB α-chain gene comprises a 232Ile variant and the FcγRIIIB α-chain gene comprises an NA2 variant.

In one embodiment, the genetic modifications comprise a replacement of syntenic genomic sequences of mouse and human chromosome 1. In a specific embodiment, the genetic modifications comprise a replacement of a genomic fragment comprising endogenous low affinity mouse FcγR genes with a genomic fragment comprising low affinity human FcγR genes. In another specific embodiment, the mouse genome from chromosome 1:172,889,983 to chromosome1:172,989,911 is replaced with a human genomic fragment comprising human chromosome 1:161,474,729 to chromosome1:161,620,458.

In one aspect, a genetically modified cell, non-human embryo, or non-human animal is provided, wherein the genetic modification comprises a knockout of one or more endogenous low affinity receptor α-chain genes, and the presence of an episome comprising one or more human FcγR α-chain genes. In a specific embodiment, the cell, embryo, or animal expresses a functional FcR γ-chain. In a specific embodiment, the episome is a mini chromosome. In one embodiment, the functional FcR γ-chain is endogenous to the cell, embryo, or animal.

In one aspect, a genetically modified mouse is provided, comprising a replacement of a low affinity mouse FcγR α-chain gene with a low affinity human FcγR α-chain gene, the mouse comprises a mouse FcRγ-chain gene, and the mouse expresses a functional human low affinity FcγR receptor. In one embodiment, the functional low affinity FcγR receptor is expressed on a cell type in which the low affinity FcγR receptor is expressed in humans. In a specific embodiment, the functional human low affinity FcγR receptor is FcγRIIIA and the FcγRIIIA is expressed on NK cells.

In one embodiment, the mouse comprises a deletion of two mouse FcγR α-chain genes. In another embodiment, the mouse comprises a deletion of three mouse FcγR α-chain genes.

In one embodiment, the mouse comprises a replacement of three mouse FcγR α-chain genes with at least one human FcγR α-chain gene. In another embodiment, the mouse comprises a replacement of two mouse FcγR α-chain genes with at least one human FcγR α-chain gene. In a specific embodiment, the mouse comprises a replacement of three mouse FcγR α-chain genes with at least two human FcγR α-chain genes. In another specific embodiment, the three mouse FcγR α-chain genes are replaced with three human FcγR α-chain genes. In another specific embodiment, the mouse comprises a replacement of two mouse FcγR α-chain genes with at least two human FcγR α-chain genes. In yet another specific embodiment, the two mouse FcγR α-chain genes are replaced with at least three human FcγR α-chain genes.

In one embodiment, the low affinity mouse FcγR α-chain gene is selected from an FcγRIIB, FcγRIV, FcγRIII α-chain gene, and a combination thereof.

In one embodiment, the low affinity human FcγR α-chain gene is selected from an FcγRIIA, FcγRIIB, FcγRIIC, FcγRIIIA, FcγRIIIB α-chain gene, and a combination thereof. In one embodiment, the low affinity human FcγR α-chain gene is selected from an FcγRIIA, an FcγRIIIA α-chain gene, and a combination thereof. In one embodiment, the low affinity human FcγR α-chain gene is selected from an FcγRIIB, FcγRIIC, an FcγRIIIB α-chain gene, and a combination thereof.

In one embodiment, the low affinity mouse FcγRIV α-chain gene and the FcγRIII α-chain gene are replaced with at least one human FcγR α-chain gene. In one embodiment, the low-affinity mouse FcγRIV α-chain gene and the FcγRIIB α-chain gene are replaced with at least one human FcγR α-chain gene. In one embodiment, the low affinity mouse FcγRIIB α-chain gene and the FcγRIIIB α-chain gene are replaced with at least one human FcγR α-chain gene. In a specific embodiment, the at least one human FcγR α-chain gene is selected from an FcγRIIA, FcγRIIB, FcγRIIC, FcγRIIIA, FcγRIIIB α-chain gene, and a combination thereof. In another specific embodiment, the at least one human FcγR α-chain gene is selected from an FcγRIIA, an FcγRIIIA α-chain gene, and a combination thereof. In another specific embodiment, the at least one human FcγR α-chain gene is selected from an FcγRIIB, FcγRIIC, FcγRIIIB α-chain gene, and a combination thereof. In another specific embodiment, the mouse α-chain genes are replaced with the following human FcγR α-chain genes: FcγRIIA and FcγRIIIA. In yet another specific embodiment, the mouse α-chain genes are replaced with the following human FcγR α-chain genes: FcγRIIB, FcγRIIC and FcγRIIIB.

In one aspect, a genetically modified mouse is provided, comprising a low affinity human FcγR α-chain and a mouse FcR γ-chain subunit, wherein the mouse expresses the human FcγR α-chain on a cell selected from a neutrophil, an eosinophil, a basophil, a monocyte, a macrophage, a platelet, a Langerhans cell, a dendritic cell, an NK cell, a mast cell, a B cell, a T cell, and a combination thereof. In one embodiment, the mouse expresses a human FcγRIIA α-chain on a cell selected from a neturophil, a macrophage, an eosinophil, a platelet, a dendritic cell, a Langerhans cell, and a combination thereof. In one embodiment, the mouse is capable of phagocytosis, ADCC and cellular activation initiated or mediated through the expressed human FcγRIIA α-chain. In one embodiment the mouse expresses a human FcγRIIIA α-chain on a cell selected from a macrophage, an NK cell, a monocyte, a mast cell, an eosinophil, a dendritic cell, a Langerhans cell, at least one T cell type, and a combination thereof. In one embodiment, the mouse is capable of ADCC mediated through the human FcγRIIIA α-chain expressed on NK cells. In a specific embodiment, the mouse exhibits hFcγRIIIA-mediated ADCC in response to an antibody comprising a human Fc.

In one embodiment, the mouse expresses both a human FcγRIIA α-chain and a human FcγRIIIA α-chain. In one embodiment, the human FcγRIIA α-chain is expressed on platelets and the human FcγRIIIA α-chain is expressed on NK cells. In one embodiment, the mouse is capable of ADCC mediated by an antibody comprising a human Fc, wherein the mediation is through either the human FcγRIIA α-chain or through the human FcγRIIIA α-chain expressed on the surface of accessory cells. In one embodiment, the human FcγRIIA α-chain is not expressed on platelets. In a specific embodiment wherein the human FcγRIIA α-chain is not expressed on platelets, the mouse lacks or substantially lacks a human promoter sequence that operably linked to the human FcγRIIA α-chain in a human genome.

In one embodiment, the mouse expresses a human FcγRIIB α-chain on a cell selected from a B cell, a mast cell, a basophil, a macrophage, an eosinophil, a neutrophil, a dendritic cell, a Langerhans cell, and a combination thereof. In a specific embodiment, the mouse expresses a human FcγRIIB α-chain on a B cell and a mast cell. In another specific embodiment, the mouse is capable of endocytosis of immune complexes mediated through the expressed human FcγRIIB α-chain. In one embodiment, the mouse expresses a human FcγRIIC α-chain on a cell selected from a neutrophil, a macrophage, an eosinophil, a platelet, a dendritic cell, a Langerhans cell, and a combination thereof. In a specific embodiment, the mouse is capable of phagocytosis, ADCC and cellular activation initiated through the expressed human FcγRIIC α-chain.

In one embodiment, the mouse expresses a human FcγRIIIB α-chain on neutrophils and eosinophils. In a specific embodiment, the mouse is capable of cellular activation, phagocytosis, ADCC and degranulation, wherein the activation, phagocytosis, ADCC, and degranulation are mediated through the expressed human FcγRIIIB α-chain.

In one aspect, a mouse is provided that comprises a deletion of the endogenous FcγRIIB, FcγRIV and FcγRIII genes and insertion of human FcγRIIA, FcγRIIB, FcγRIIC, FcγRIIIA, and FcγRIIIB genes, and wherein the mouse comprises a functional mouse FcR γ-chain gene.

In one embodiment, the mouse comprises a deletion of the α-chains encoded by endogenous FcγRIIB, FcγRIV and FcγRIII genes and insertion of the α-chains encoded by human FcγRIIA, FcγRIIB, FcγRIIC, FcγRIIIA, and FcγRIIIB genes.

In one embodiment, the insertion of the human FcγRIIA, FcγRIIB, FcγRIIC, FcγRIIIA, and FcγRIIIB α-chain genes is at a random location within the mouse genome.

In one embodiment, the insertion of the human FcγRIIA, FcγRIIB, FcγRIIC, FcγRIIIA, and FcγRIIIB α-chain genes is at the endogenous mouse low affinity FcγR α-chain locus.

In one embodiment, the mouse expresses human FcγRIIIA on NK cells and macrophages. In a specific embodiment, all or substantially all NK cells from a splenocyte sample of the mouse express human FcγRIIIA. In a specific embodiment, all or substantially all macrophages from a splenocyte sample of the mouse express human FcγRIIIA.

In one embodiment, the mouse expresses a human FcγR selected from human FcγRIIA, human FcγRIIIA, and a combination thereof, on a cell type selected from neutrophils, macrophages, and a combination thereof. In a specific embodiment, the mouse expresses human FcγRIIA and human FcγRIIIA on all or substantially all neutrophils and macrophages of a splenocyte sample from the mouse.

In one embodiment, the mouse expresses human FcγRIIB and human FcγRIIIB on B cells and neutrophils of B cells from a B cell-gated splenocyte sample from the mouse. In a specific embodiment, the mouse expresses FcγRIIIB and FcγRIIB on all or substantially all B cells and neutrophils from a B cell-gated splenocyte sample from the mouse.

In one embodiment, the mouse further comprises a humanized CD20 gene. In one embodiment, the mouse that further comprises the humanized CD20 gene following treatment with an anti-CD20 binding protein that comprises an Fc exhibits depletion (in vivo) of B cells. In one embodiment, the depletion is in a compartment selected from bone marrow, blood, lymph node, spleen, and a combination thereof. In one embodiment, the Fc is a human Fc. In one embodiment, the Fc is a mouse Fc. In one embodiment, the anti-CD20 binding protein is an anti-CD20 antibody.

In one aspect, a cell is provided comprising a genetic modification as described herein. In one embodiment, the cell is selected from an embryonic stem (ES) cell, a pluripotent cell, an induced pluripotent cell, and a totipotent cell. In one embodiment, the cell is selected from a mouse cell and a rat cell. In a specific embodiment, the cell is an ES cell. In a more specific embodiment, the cell is a mouse ES cell.

In one aspect, a non-human embryo is provided, comprising a genetic modification as described herein. In one embodiment, the non-human embryo is selected from a mouse embryo and a rat embryo.

In one aspect, a method is provided for determining efficacy of a therapeutic. In one embodiment, the therapeutic is an antibody (e.g., mono-, bi-, tri-, multispecific) comprising a human Fc. In one embodiment, the therapeutic is a human antibody. In one embodiment, the efficacy is efficacy of therapeutic-mediated cell killing (e.g., ADCC). In a specific embodiment, the human therapeutic is a fusion protein comprising an Fc of a human immunoglobulin heavy chain. In one embodiment, the therapeutic is administered to a mouse as described herein and a level of therapeutic-dependent ADCC is measured. In one embodiment, the mouse is used to assess the ADCC activity of a therapeutic by administering the therapeutic to the mouse and then detecting (e.g., in vitro from a sample (e.g., blood) taken from the animal) binding of the therapeutic to a human low affinity FcγR on an FcγR-expressing cell. In a specific embodiment, accessory cells of the mouse are isolated from the mouse and tested for the ability, in the presence and absence of the therapeutic, to mediate therapeutic-dependent ADCC.

In one aspect, a method is provided for determining whether a low affinity FcγR is associated with a human disease or disorder, comprising a step of determining a trait associated with the human disease or disorder in a mouse according to the invention. In one embodiment, the trait is a phenotype associated with the absence or loss of a function of one or more low affinity FcγRs. In a specific embodiment, the disease or disorder is an autoimmune disease or disorder. In a specific embodiment, the autoimmune disease or disorder is selected from Rheumatoid Arthritis (RA), Systemic Lupus Erythematosus (SLE), type I diabetes, Guillain-Barré syndrome, sclerosis, multiple sclerosis, Goodpasture's syndrome, Wegener's Granulomatosis and experimental autoimmune encephalomyelitis (EAE). In a specific embodiment, the mouse comprises a polymorphism in a low affinity FcγR, and the trait is selected from an enhanced ability to mediate ADCC in comparison to the majority of the human population that does not bear the polymorphism, and a reduced ability to mediate ADCC in comparison to the majority of the human population that does not bear the polymorphism.

In one aspect, a method for making an anti-human FcR α-chain antibody in a mouse is provided, comprising exposing a mouse according to the invention to a human FcR as described herein. In one embodiment, an antibody that recognizes the human FcR is isolated from the mouse. In another embodiment, a nucleic acid sequence that encodes all or part of a variable region of an antibody that recognizes the human FcR is identified and cloned.

In one aspect, a method for determining ability of anti-human FcR antibodies to target molecules to FcR-expressing cells for phagocytosis of the target molecule is provided, comprising exposing a mouse as described herein to an agent comprising an anti-human FcR antibody, and measuring phagocytosis of the target molecule.

In one aspect, a method is provided for making an antibody, in a mouse, to an antigen that is poorly immunogenic in a mouse that is wild type with respect to one or more FcγRs, comprising exposing a mouse as described herein that lacks a mouse low affinity FcR but expresses an FcγR γ-chain to the antigen that is poorly immunogenic in the mouse that is wild type with respect to one or more FcγRs, and identifying an antibody that recognizes the poorly antigenic antigen. In one embodiment, the method comprises isolating the antibody from the mouse. In another embodiment, a nucleic acid sequence that encodes all or part of a variable region of the antibody is identified and cloned.

In one aspect, a method for making a mouse capable of making antibodies comprising human variable regions is provided, comprising a step of breeding a first mouse as described herein with a second mouse that comprises (a) one or more human immunoglobulin variable region gene segments and one or more human constant region genes; or, (b) one or more human immunoglobulin variable region gene segments operably linked to a mouse constant region gene, wherein the human gene segments replace variable region gene segments at the mouse variable region gene segment locus.

In one embodiment, the second mouse (a) comprises a transgene that comprises one or more human immunoglobulin light chain variable region gene segments and a human light chain constant gene, and a transgene that comprises one or more human immunoglobulin heavy chain variable region gene segments and one or more human heavy chain constant genes. In one embodiment, the transgene that comprises one or more human immunoglobulin heavy chain variable region gene segments comprises two or more heavy chain constant genes and is capable of class switching. In a specific embodiment, the mouse comprises an inactivated endogenous light chain locus and/or an inactivated endogenous heavy chain locus. In a specific embodiment, the mouse comprises a deletion of an endogenous light chain locus and/or a deletion of an endogenous heavy chain locus.

In one embodiment, the second mouse (b) comprises human heavy and human light variable region gene segments, at the heavy an light mouse loci, respectively.

In one aspect, a method is provided for selecting an anti-tumor antibody, comprising a step of determining the ability of an antibody to mediate ADCC, wherein the ability of the antibody to mediate ADCC is tested by determining ADCC mediated by a cell of a mouse as described herein, and the antibody is selected if it mediates ADCC employing a cell of a genetically modified mouse as described herein. In a specific embodiment, binding of the antibody to the cell of the genetically modified mouse is determined, and the anti-tumor antibody is selected for its ability to bind a human FcγR on the cell. In a specific embodiment, the human FcγR is a low affinity FcγR.

In one embodiment, the anti-tumor antibody is identified by its enhanced ability to mediate ADCC through a cell of the mouse as compared to ability of the anti-tumor antibody to mediate ADCC through a cell of a wild type mouse. In a specific embodiment, the anti-tumor antibody is identified by its ability to mediate ADCC through NK cells. In a specific embodiment, the NK cells express human FcγRIIIA.

In one embodiment, a method is provided for selecting an anti-tumor agent, comprising a step of administering an agent comprising a human Fc or a modified human Fc to a first non-human animal wherein the first non-human animal is genetically modified in accordance with the invention and comprises a human tumor; a step of administering the agent to a second non-human animal comprising the tumor; and determining the ability of the first non-human animal and the second non-human animal to retard growth of the human tumor following administration of the agent, wherein the agent is selected as an anti-tumor agent if it exhibits an enhanced ability to retard growth of the human tumor in the first non-human animal but not in the second non-human animal.

In one embodiment, the first non-human animal is modified to comprise a deletion of an endogenous FcR α-subunit, and is modified to comprise a human FcR α-subunit selected from the group consisting of an FcγRIIA α-subunit, an FcγRIIB α-subunit, an FcγRIIC α-subunit, an FcγRIIIA α-subunit, an FcγRIIIB α-subunit, and a combination thereof. In one embodiment, the second animal is a wild type animal. In one embodiment, the first non-human animal expresses an endogenous FcR γ-chain.

In one embodiment, the first non-human animal expresses a functional endogenous FcγRI.

In one aspect, a method is provided for making a mouse that lacks a low affinity mouse FcγR, expresses a functional FcR γ-chain, and comprises genes encoding α-chains of the human FcγRIIA, FcγRIIB, FcγRIIC, FcγRIIIA, and FcγRIIIB, comprising a step of replacing the low affinity mouse FcγR α-chains with human FcγR α-chains, at the mouse FcγR α-chain locus.

In one embodiment, a first step comprises deleting the α-chains of the endogenous FcγRIIB, FcγRIV and FcγRIII genes and inserting the α-chains of the human FcγRIIA and FcγRIIIA genes; a second step comprises inserting the α-chains of the human FcγRIIB, FcγRIIC and FcγRIIIB genes into the mouse genome that results from the first step; wherein the mouse comprises a functional mouse FcR γ-chain gene. In a specific embodiment, the α-chains of the human FcγRIIB, FcγRIIC and FcγRIIIB genes of the second step are inserted 5' relative to the α-chains of the human FcγRIIA and FcγRIIIA genes of the first step.

In one aspect, a method for determining cell killing by a human therapeutic in a non-primate is provided, comprising a step of exposing a cell, non-human embryo, or non-human animal to a human therapeutic that comprises a human Fc, wherein the cell, embryo, or animal comprises a functional FcR γ-chain and comprises a replacement of one or more endogenous low affinity FcγR α-chain genes with one or more human FcγR α-chains, and determining the ability of the human therapeutic to mediate cell killing through a low affinity human FcγR of the cell, embryo, or animal.

In one embodiment, the non-primate is a mouse. In a specific embodiment, endogenous mouse FcγR α-chain genes FcγRIIB, FcγRIV and FcγRIII are replaced with human FcγR α-chain genes FcγRIIA, FcγRIIB, FcγRIIC, FcγRIIIA, and FcγRIIIB.

In one embodiment, the cell is selected from a B cell, a mast cell, a basophil, a macrophage, an eosinophil, a neutrophil, a dendritic cell, a Langerhans cell, and a combination thereof. In a specific embodiment, the cell is an NK cell and NK cell-mediated ADCC by a human or a humanized antibody is determined. In a specific embodiment, the low affinity human FcγR is a human FcγRIIIA.

In one aspect, a method for determining therapeutic-dependent thrombosis is provided, comprising exposing a first non-human animal that expresses a human FcγRIIA on a platelet to a therapeutic; exposing a second non-human animal that does not express the human FcγRIIA on a platelet to said therapeutic; measuring in the first non-human animal and in the second non-human animal an amount of therapeutic-dependent thrombosis; and, determining a difference in therapeutic-dependent thrombosis.

In one embodiment, the non-human animal is selected from a mouse and a rat.

In one embodiment, the determined difference in therapeutic-dependent thrombosis is employed to identify a risk associated with administering the therapeutic to a human. In one embodiment, the determined difference results in a change of administration of the therapeutic to a human patient in need thereof.

DETAILED DESCRIPTION

The invention is not limited to particular methods, and experimental conditions described, as such methods and conditions may vary. The terminology used herein is for the purpose of describing particular embodiments only, and is not intended to be limiting, since the scope of the present invention will be limited only by the claims.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, particular methods and materials are now described. All publications mentioned herein are incorporated herein by reference in their entirety.

The phrase "targeting construct" includes a polynucleotide molecule that comprises a targeting region. A targeting region comprises a sequence that is substantially homologous to a sequence in a target cell, tissue or animal and provides for integration of the targeting construct into a position within the genome of the cell, tissue or animal. In a specific embodiment, the targeting construct further comprises a nucleic acid sequence or gene of particular interest, a selectable marker, control and or regulatory sequences, and other nucleic acid sequences that allow for recombination mediated through the exogenous addition of proteins that aid in or facilitate recombination involving such sequences. In another specific embodiment, the targeting construct further comprises a gene of interest, wherein the gene of interest is a heterologous gene that encodes a protein that has a similar function as a protein encoded by the endogenous sequence.

The term "replacement" includes wherein a DNA sequence is placed into a genome of a cell in such a way as to replace a sequence within a genome, at the locus of the genomic sequence, with a heterologous sequence (e.g., a human sequence in a mouse), unless otherwise indicated. The DNA sequence so placed may include one or more regulatory sequences that are part of source DNA used to obtain the sequence so placed (e.g., promoters, enhancers, 5'- or 3'-untranslated regions, etc.). For example, in various embodiments, the replacement is a substitution of an endogenous sequence for a heterologous sequence that results in the production of a gene product from the DNA sequence so placed (comprising the heterologous sequence), but not expression of the endogenous sequence; the replacement is of an endogenous genomic sequence with a DNA sequence that encodes a protein that has a similar function as a protein encoded by the endogenous genomic sequence (e.g., the endogenous genomic sequence encodes a low affinity mouse FcγR receptor, and the DNA fragment encodes one or more human low affinity FcγR receptors, such as, e.g., a human FcγRIIC and/or an FcγRIIIB).

The term "FcγR" includes a receptor for an Fc, e.g., an Fc portion of an IgG immunoglobulin. The FcγR genes include an α-chain that is expressed on the surface of the cell and serves as a ligand-binding domain, and associates with either a homodimer of the FcR γ-chain or a heterodimer of the FcR γ-chain and the δ-chain. There are several different FcγR genes and they can be categorized into low affinity and high affinity types according to preferential binding to IgG in immune complexes. Low affinity FcγR genes in humans include FcγRIIA, FcγRIIB, FcγRIIC, FcγRIIIA and FcγRIIIB and within most of these genes naturally occurring genetic differences, or polymorphisms, have been described in human subjects with autoimmune diseases. Persons of skill upon reading this disclosure will recognize that one or more endogenous low affinity FcγR genes in a genome (or all) can be replaced by one or more heterologous low affinity FcγR genes (e.g., variants or polymorphisms such as allelic forms, genes from another species, chimeric forms, etc.).

The phrase "allelic variants" includes variations of a normal sequence of a gene resulting in a series of different forms of the same gene. The different forms may comprise differences of up to, e.g., 20 amino acids in the sequence of a protein from a gene. For example, alleles can be understood to be alternative DNA sequences at the same physical gene locus, which may or may not result in different traits (e.g., heritable phenotypic characteristics) such as susceptibility to certain diseases or conditions that do not result in other alleles for the same gene or result in varying degrees in the other alleles.

An "accessory cell" includes an immune cell that is involved in the effector functions of the immune response. Exemplary immune cells include a cell of lymphoid or myeloid origin, e.g., lymphocytes, natural killer (NK) cells, monocytes, macrophages, neutrophils, eosinophils, basophils, platelets, Langerhans cells, dendritic cells, mast cells etc. Accessory cells carry out specific functions of the immune system through receptors, e.g., FcRs, expressed on their surfaces. In a specific embodiment, an accessory cell is capable of triggering ADCC mediated through an FcR, e.g., a low affinity FcγR, expressed on the cell surface. For example, macrophages expressing FcRs are involved in phagocytosis and destruction of antibody-coated bacteria. Accessory cells might also be capable of releasing an agent that mediates other immune processes. For example, mast cells can be activated by antibody bound to FcRs to release granules, e.g., inflammatory molecules (e.g., cytokines) at a site of infection. In various other embodiments, the expression of FcRs on accessory cells can be regulated by other factors (e.g., cytokines). For example, FcγRI and FcγRIII expression can be inducted by stimulation with interferon-γ (IFN-γ).

Mouse and Human FcRs

The receptors for the Fc (i.e., constant) regions of immunoglobulins (FcRs) play an important role in the regulation of the immune response. FcRs are present on accessory cells of the host's immune system to effectively dispose of foreign antigens bound by an antibody. FcRs also play important roles in balancing both activating and inhibitory responses of the accessory cells of the immune system. FcRs are involved in phagocytosis by macrophages, degranulation of mast cells, uptake of antibody-antigen complexes and modulation of the immune response, as well as other immune system processes.

In mice and humans, distinct FcRs are differentially expressed on the surface of different accessory cells that are each specific for the immunoglobulin isotypes present in the expressed antibody repertoire. For example, immunoglobulin G (IgG) antibodies mediate effector functions through IgG receptors (FcγRs). FcγRs have been classified into three groups: high affinity activating FcγRI (CD64), low affinity inhibitory FcγRII (CD32) and low affinity activating FcγRIII (CD16). Although each group is present in both mice and humans, the number of isoforms and subsets of immune cells on which they are present are different. For example, FcγRIIA and FcγRIIIB are expressed on accessory cells in humans but are reportedly absent from mice. Further, affinities of the different IgG isotypes (e.g., IgG1) for each FcγR is different in mice and humans.

Activation or inhibition of cell signaling through FcγRs and the effector functions associated with antibody binding to FcγRs are believed to be mediated by specific sequence motifs of intracellular domains of FcγRs, or of the subunits of co-receptors. Activating receptors are most commonly associated with the common γ-chain (FcR γ-chain) which contains an immunoreceptor tyrosine-based activation motif (ITAM). ITAMs contain a specific sequence of about 9-12 amino acids that include tyrosine residues that are phosphorlyated in response to antibody binding to an FcR. Phosphorylation leads to a signal transduction cascade. Mice that lack a gene encoding an FcR γ-chain (FcR γ-chain KO) have been reported (e.g., see Takai et al. (1994) FcR γ Chain Depletion Results in Pleiotrophic Effector Cell Defects, Cell 76:519-529; van Vugt et al. (1996) FcR γ-Chain Is Essential for Both Surface Expression and Function of Human FcγRI (CD64) In Vivo, Blood 87(9):3593-3599; and Park et al. (1998) Resistance of Fc Receptor-deficient Mice to Fatal Glomerulonephritis, J. Clin. Invest. 102(6):1229-1238). The FcR γ-chain is reportedly essential for proper surface expression and function (e.g., signal transduction, phagocytosis, etc.) of most of the FcRs; FcR γ-chain KO mice lack FcγRI according to some reports. However, other reports reveal that FcR γ-chain KO mice indeed express FcγRI on the surface of certain accessory cells, and the FcγRI expressed reportedly appears functional in that it binds IgG in mice in the absence of expressed FcR γ-chain (Barnes et al. (2002) FcγRI-Deficient Mice Show Multiple Alterations to Inflammatory and Immune Responses, Immunity 16:379-389).

In contrast, FcγRIIB is an inhibitory receptor that contains an immunoreceptor tyrosine-based inhibitory motif (ITIM) in its cytoplasmic domain. Like ITAMs, ITIMs are sequence motifs that include phosphorylatable tyrosine residues. However, downstream events following phosphorylation of an ITM lead to inhibition, not activation, of immune cell functions. Mice deficient in FcγRIIB reportedly exhibit an increased antibody response in comparison to wild type mice (Takai et al. (1996) Augmented humoral and anaphylactic responses in FcgRII-deficient mice, Nature 379:346-349), an observation that supports the role of FcγRIIB as a downregulator of the B cell antibody response.

In humans, FcγRIIA, FcγRIIB, FcγRIIC, FcγRIIIA and FcγRIIIB are considered the classical low affinity FcγR genes and are located together on the same chromosome (Su et al. (2002) Genomic organization of classical human low-affinity Fcγ receptor genes, Genes and Immunity 3 (Supple 1):551-556). These genes exhibit several polymorphisms associated with distinct phenotypes, e.g., an alteration of ligand binding and function of the receptor. Some polymorphisms are associated with autoimmune diseases, e.g., systemic lupus erythematosus (SLE), rheumatoid arthritis (RA), and multiple sclerosis (MS). Transgenic mice for different human FcγRs (hFcγRs) have been developed and used as disease models, generating high affinity antibodies, testing therapeutic antibodies for ability to elicit specific cellular responses, screening compounds that ameliorate aberrant immune responses, etc. (e.g., see Heijnen et al. (1996) A Human FcgRI/CD64 Transgenic Model for In Vivo Analysis of (Bispecific) Antibody Therapeutics, J. Hematother. 4:351-356; Heijnen and van de Winkel (1996) Antigen Targeting to Myeloid-specific Human FcgRI/CD64 Triggers Enhanced Antibody Responses in Transgenic, J. Clin. Invest. 97(2):331-338; U.S. Pat. Nos. 6,111,166, 6,676, 927, 7,351,875, 7,402,728, and 7,416,726).

Despite the significant roles of the FcRs in providing the bridge between antibodies and accessory cells of the immune system, no model system currently exists in which all the low affinity hFcγRs are expressed. A mouse in which all the low-affinity hFcγRs are co-expressed—including mice that lack endogenous mouse FcγRs—in various embodiments could be used to accurately reflect effects of a human antibody therapeutic, including ADCC-mediated effects. Such a mouse would serve as a vital tool in the engineering, analysis and evaluation of therapeutic antibodies for treatment of human diseases such as, e.g., RA, type I diabetes, SLE, and autoimmunity, by providing an animal model capable of achieving a more accurate assessment of immunological processes in humans, particularly in the context of testing human antibody therapeutics. The mouse will also be a valuable source of cells bearing the low affinity receptors, which cells can be used in in vitro assays for assessing therapeutic-dependent cell killing for therapeutics that bind the low affinity receptors, and thus for identifying useful human therapeutics.

Endogenous Low Affinity FcγR Gene Deficient Mice

Genetically modified non-human animals are provided that do not express endogenous low affinity mouse FcγR genes, but that express an endogenous mouse FcR γ-chain. In various embodiments, the FcR γ-chain is expressed in a distribution (i.e., in cell types) and at a level in the mouse that is the same or substantially the same as in a wild type mouse. Endogenous low affinity FcγR genes can be expressed either on the surface of immune cells or in a soluble manner in the periphery of the animals. Genetic modifications for making a non-human animal that does not express endogenous low affinity mouse FcγR genes are conveniently described by using the mouse as an illustration. A genetically modified mouse according to the invention can be made in a variety of ways, particular embodiments of which are discussed herein.

A schematic illustration (not to scale) of low affinity mouse FcγR gene locus is provided in FIG. 1 (top) to show FcγR gene arrangement at the endogenous locus. As illustrated, low affinity mouse FcγR genes FcγRIIB, FcγRIV and FcγRIII are present together in close proximity on one chromosome. Each of these genes comprise the α-chain or ligand binding domain responsible for the binding the Fc portion of an antibody molecule.

A genetically modified mouse lacking a nucleotide sequence encoding an α-chain of the endogenous low affinity FcγR genes can be made by any method known in the art. For example, a targeting vector can be made that deletes the low affinity mouse FcγR α-chain genes with selectable marker gene. FIG. 1 illustrates a mouse genome (bottom) targeted by a targeting construct having a 5' homology arm containing sequence upstream of the endogenous low affinity FcγR α-chain locus, followed by a drug selection cassette (e.g. a neomycin resistance gene flanked by loxP sequences), and a 3' homology arm containing sequence downstream of the endogenous low affinity FcγR α-chain locus. Upon homologous recombination at the locus, the endogenous low affinity FcγR α-chain locus is replaced by a drug selection cassette (bottom of FIG. 1). The endogenous low affinity FcγR α-chain gene locus is thereby deleted resulting in a cell or non-human animal that does not express endogenous low-affinity mouse FcγR α-chain genes. The drug selection cassette may optionally be removed by the subsequent addition of a recombinase (e.g., by Cre treatment).

Genetically modifying a mouse to render an endogenous low-affinity mouse FcγR α-chain gene or genes nonfunctional, in various embodiments, results in a mouse that exhibits defects in immune responses, making the mouse useful for evaluating cooperative, as well as individual, roles of the endogenous low-affinity mouse FcγR genes in normal and disordered immune function, IgG-mediated processes, and autoimmune disease. In various embodiments, modifying the α-chains of the endogenous low-affinity mouse FcγR genes, but not the FcR γ-chain, avoids a potential reduction of other endogenous FcR genes (e.g., high affinity FcγRI) that require the FcR γ-chain for surface expression and function, thus maintaining various other immunological functions and processes mediated through γ-chain-dependent processes.

According to some reports, FcR γ-chain deficient mice lack surface expression of FcγRIII and FcγRI. However, FcγRI has reportedly been detected on the cell surface in FcR γ-chain deficient mice and is reportedly at least partially functional. In contrast, mice according to the present invention contain unmodified endogenous FcR γ-chain, which preserves natural cell surface expression patterns and cellular functions of other FcR genes that require FcR γ-chain.

In various embodiments, mice of the present invention present an advantage over other FcγR gene-deficient mice in that the genetic modifications that they bear result in the maintenance of other genes necessary for other immunological functions not entirely devoted to low affinity FcγR genes. For example, with a functional FcR γ-chain, other γ-chain-dependent proteins (e.g., FcγRI) will be able to associate with the FcR γ-chain and participate in effector cell functions in the immune response. In various genetically modified mice in accordance with the invention, it is believed that maintaining such functions (due to the presence of a functional FcRγ-chain) while deleting endogenous low affinity FcγR genes (one or more α-subunits) enables a more precise elucidation of the roles of FcRs in autoimmunity.

Low Affinity FcγR Humanized Mice

Genetically modified non-human animals are provided that express low-affinity human FcγR genes. Low affinity human FcγR genes can be expressed either on the surface of accessory cells of the animal's immune system or in a soluble manner in the periphery of the animals.

The genetic modification, in various embodiments, comprises a deletion of a functional α-chain of one or more low-affinity mouse FcγR genes, and in some embodiments a further modification comprising a replacement with two or more, with three or more, with four or more, or with five low-affinity human FcγR α-subunit genes, wherein the non-human animal expresses a functional mouse FcR γ-chain gene. Genetically modified non-human embryos, cells, and targeting constructs for making the non-human animals, non-human embryos, and cells are also provided.

Compositions and methods for making a mouse that expresses a human FcγR gene, including specific polymorphic forms or allelic variants (e.g., single amino acid differences), are provided, including compositions and method for making a mouse that expresses such genes from a human promoter and a human regulatory sequence. The methods include selectively rendering an endogenous low affinity mouse FcγR gene nonfunctional (e.g., by a deletion of its α-chain), and employing an α-chain of a low affinity human FcγR gene at the endogenous low affinity mouse FcγR gene locus to express a low affinity human FcγR α-subunit gene in a mouse. The deletion of the low affinity mouse FcγR gene is made by deletion of one or more α-chain genes, but not an FcRγ-chain gene. The approach selectively renders one or more endogenous low affinity FcγR α-chain genes nonfunctional while retaining a functional endogenous FcRγ-chain.

The endogenous FcγR α-chain replacement approach employs a relatively minimal disruption in natural FcγR-mediated signal transduction in the animal, in various embodiments, because the genomic sequence of the FcγR α-chains are replaced in a single fragment and therefore retain normal functionality by including necessary regulatory sequences. Thus, in such embodiments, the FcγR α-chain modification does not affect other endogenous FcRs dependent upon functional FcRγ-chain molecules. Further, in various embodiments, the modification does not affect the assembly of a functional receptor complex involving an FcγR α-chain and the endogenous FcR γ-chain, which is believed to be required for proper expression of some FcγR α-chains on the cell surface and for downstream signaling resulting from an activated receptor. Because the FcR γ-chain is not deleted, in various embodiments animals containing a replacement of endogenous FcγR α-chain genes with human FcγR α-chain genes should be able to process normal effector functions from antibodies through binding of the Fc portion of IgG immunoglobulins to the human FcγR α-chains present on the surface of accessory cells.

Figure 4:
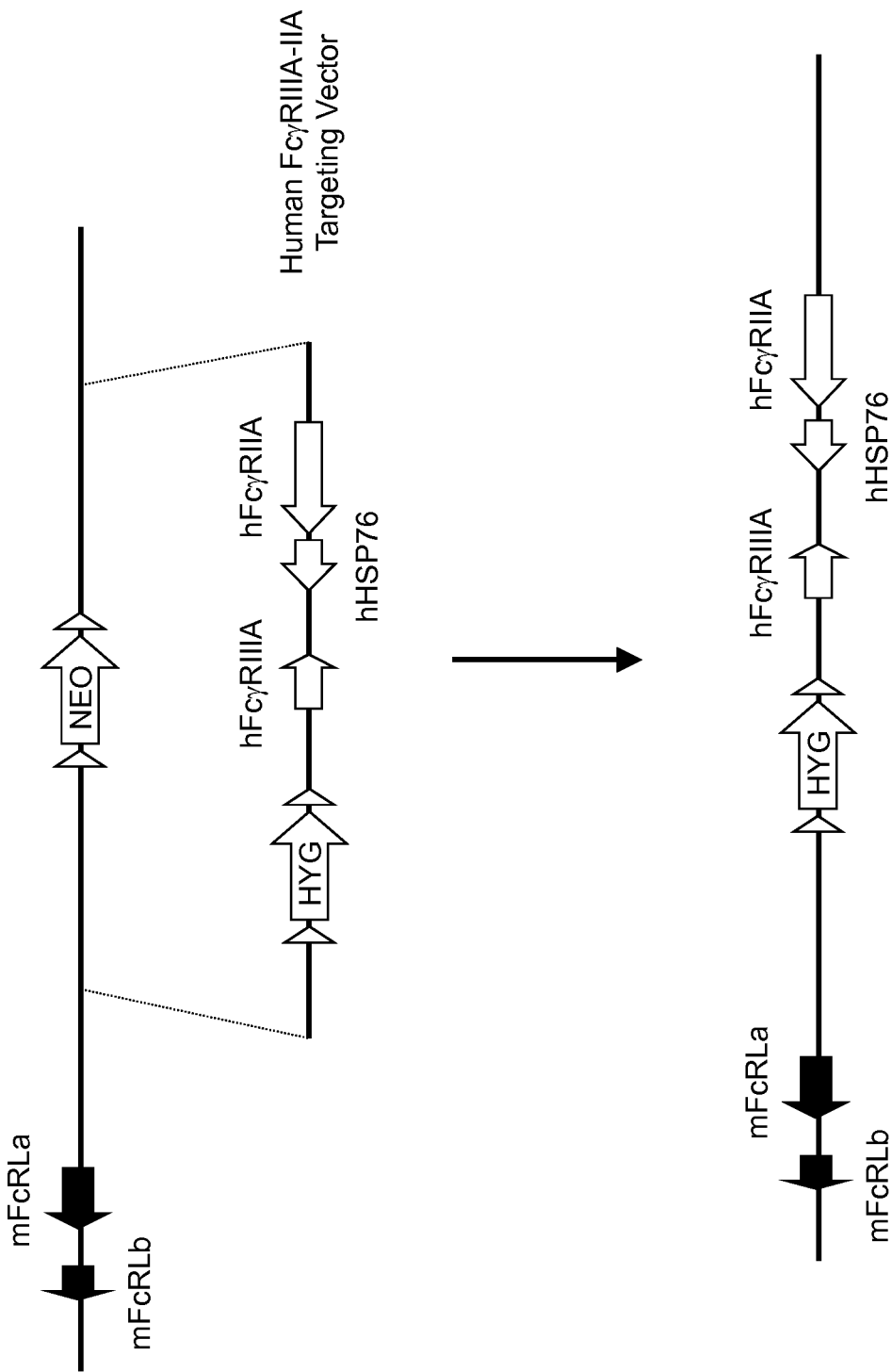
FIG. 4 is a schematic depiction of a neomycin-targeted deletion of the low-affinity mouse FcγR locus and a second targeting vector for inserting two human low affinity FcγR genes (hFcγRIIIA and hFcγRIIA) into the deleted mouse locus, which includes a hygromycin cassette flanked by site-specific recombination sites. For expression of hFcγRIIA on platelets, an extended promoter region operably linked to the hFcγRIIA gene of the Human FcγRIIIA-IIA Targeting Vector is employed; to prevent expression of hFcγRIIA on platelets, the promoter region is omitted or substantially omitted.

A schematic illustration (not to scale) of a deleted endogenous low affinity mouse FcγR gene is provided in FIG. 4 (top). As illustrated, low affinity human FcγR genes FcγRIIA and FcγRIIIA are inserted into the deleted endogenous low affinity mouse FcγR gene locus by a targeting construct (Human FcγRIIIA-IIA Targeting Vector) with a genomic fragment containing the human low affinity human FcγRIIA and FcγRIIIA genes. Each of these genes comprise the α-chain or ligand-binding domain of the human FcγR genes responsible for the binding the Fc portion of an antibody molecule.

A genetically modified mouse that expresses low affinity human FcγR genes at the endogenous low affinity mouse FcγR locus can be made by any method known in the art. For example, a targeting vector can be made that introduces low affinity human FcγR genes (e.g., FcγRIIA and FcγRIIIA) with a selectable marker gene. FIG. 4 illustrates a mouse genome comprising a deletion of the endogenous low affinity FcgR locus (top). As illustrated, the targeting construct contains a 5' homology arm containing sequence upstream of the endogenous low affinity mouse FcγR locus, followed by a drug selection cassette (e.g., a hygromycin resistance gene flanked on both sides by loxP sequences), a genomic fragment containing a human FcγRIIA gene, human HSP76 gene and human FcγRIIIA gene, and a 3' homology arm containing sequence downstream of the endogenous low affinity mouse FcγR locus. Upon homologous recombination at the deleted locus, the drug selection cassette is replaced by the sequence contained in the targeting vector (bottom of FIG. 4). The endogenous low affinity FcγR gene locus is thus replaced with low affinity human FcγR genes resulting in a cell or animal that expresses low-affinity human FcγR genes. The drug selection cassette may optionally be removed by the subsequent addition of a recombinase (e.g., by Cre treatment).

For expression of hFcγRIIA on platelets, the targeting construct Human hFcγRIIA-IIA Targeting Vector comprises an extended sequence that includes, e.g., all or substantially all of the human promoter region operably linked to the hFcgRIIA gene in a human genome. For preventing expression of hFcγRIIA on platelets, the targeting construct lacks all or substantially all of the human promoter region operably linked to the hFcγRIIA gene in a human.

Further modifications to the chimeric locus (bottom of FIG. 4) can be achieved using similar techniques as described for replacement with two human FcγR genes. The modification to replace the endogenous low affinity FcγR gene locus with two human FcγR genes can further provide a starting point for incorporation of other low affinity human FcγR genes. For example, a schematic illustration (not to scale) of an endogenous low affinity FcγR locus replaced with two human low affinity FcγR genes is provided in FIG. 6 (top). As illustrated, low affinity human FcγR genes FcγRIIB, FcγRIIC and FcγRIIIB are inserted into the modified endogenous low affinity mouse FcγR gene locus by another targeting construct (Human FcγRIIIB-IIIB-IIC Targeting Vector) with a genomic fragment containing the low affinity human FcγRIIB, FcγRIIC and FcγRIIIB genes. Each of these genes comprise the α-chain or ligand-binding domain of the human FcγR genes responsible for the binding the Fc portion of an antibody molecule.

Figure 6:
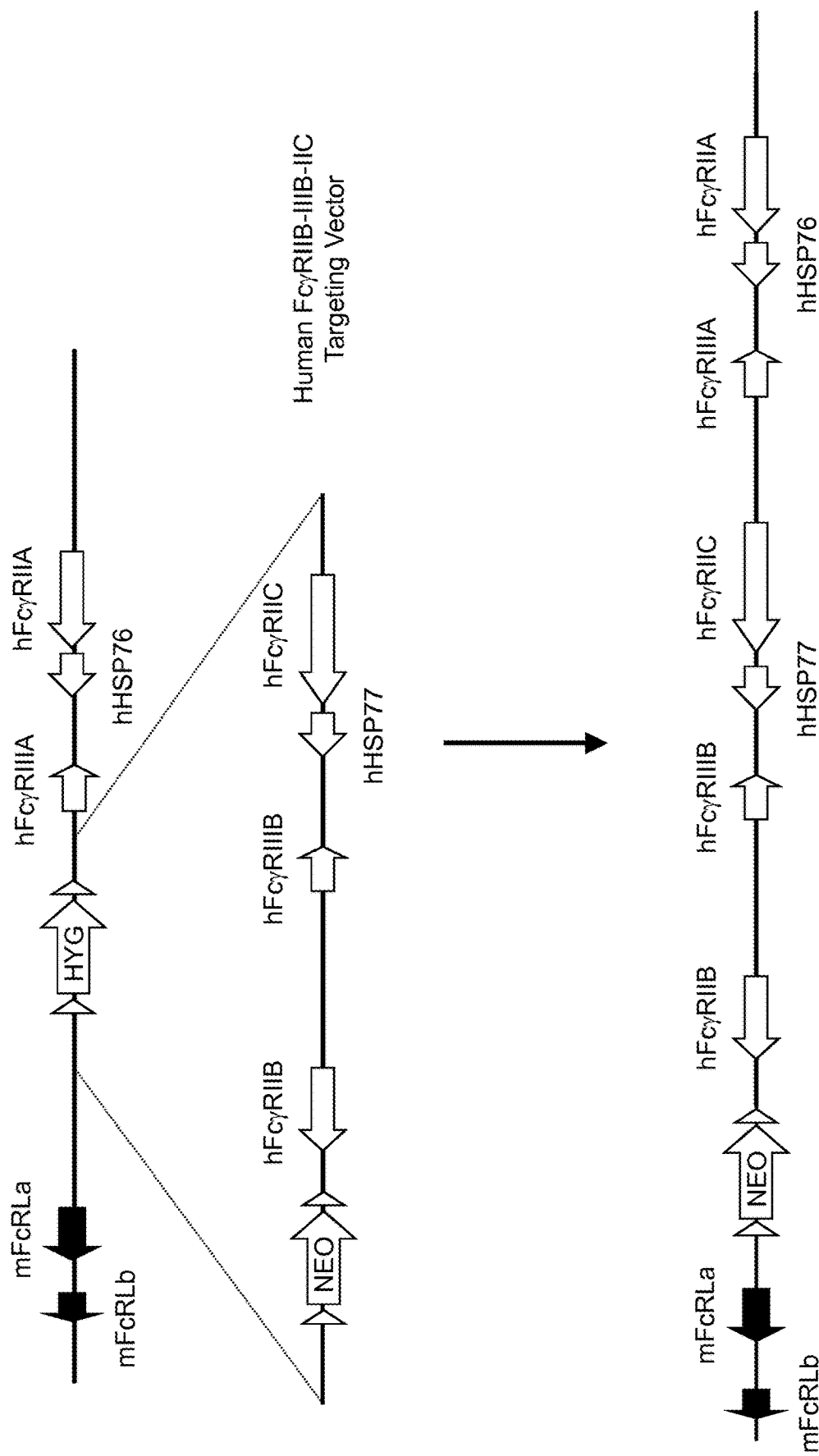
FIG. 6 is a schematic depiction of a hygromycin-targeted deletion of the low affinity mouse FcγR locus including an insertion of two low affinity human FcγR genes (hFcγRIIIA and hFcγRIIA) and a third targeting vector for inserting three additional low affinity human FcγR genes (hFcγRIIIB, hFcγRIIIB and hFcγRIIC) and a neomycin cassette flanked by site-specific recombination sites.

A genetically modified mouse that expresses five low affinity human FcγR genes at the endogenous low affinity mouse FcγR locus can be made by any method known in the art. For example, a targeting vector can be made that introduces low affinity human FcγR genes (e.g., FcγRIIB, FcγRIIC and FcγRIIIB) with a selectable marker gene. FIG. 6 illustrates a mouse genome comprising a replacement of the endogenous low affinity FcγR locus with two low affinity human FcγR genes (top). As illustrated, the targeting construct contains a 5' homology arm containing sequence upstream of the endogenous low affinity mouse FcγR locus, followed by a drug selection cassette (e.g., a neomycin resistance gene flanked on both sides by loxP sequences), a genomic fragment containing a human FcγRIIB gene, a human FcγRIIIB, a human HSP77 gene, a human FcγRIIC gene, followed by a 3' homology arm containing sequence upstream of the low affinity human FcγRIIIA gene present at the endogenous locus. Upon homologous recombination at the modified locus, a human FcγRIIB, FcγRIIIB and FcγRIIC gene are inserted 5' to the human FcγRIIIA and FcγRIIA genes previously present at the endogenous low affinity FcγR gene locus by the sequence contained in the targeting vector (bottom of FIG. 6). The modified endogenous low affinity FcγR gene locus is thus further modified to incorporate three additional low affinity human FcγR genes resulting in a cell or animal that expresses five low-affinity human FcγR genes. The drug selection cassette may optionally be removed by the subsequent addition of a recombinase (e.g., by Cre treatment). FIG. 6 (bottom) shows the structure of the resulting locus, which will express five low affinity human FcγR genes that can be detected on the surface of accessory cells of the animal's immune system and independently associate, as appropriate, with an endogenous FcRγ-chain.

Experimental Models of FcγR Deficient Mice and FcγR Humanized Mice

Genetically modified non-human animals that do not express endogenous low affinity mouse FcγR genes are useful, e.g., to elucidate the various functions of the individual low affinity FcγR genes in the immune response, to measure the efficacy of a human therapeutic antibody via cell-mediated immunity (e.g., ADCC), to determine an FcγR's role in immune diseases or disorder, to serve as models of immune diseases or disorders, to generate antibodies against one or more FcγR proteins, and to serve as breeding mates to generate other genetically modified mice of interest.

In one embodiment, a mouse according to the invention can be used to determine a cytotoxic effect lost (in comparison to a wild type mouse) by a mouse that does not express low affinity FcγR genes by administering an agent to such a mouse, where the agent is known to trigger an FcγR-dependent cytotoxic effect in wild type mice. In one embodiment, a mouse of the present invention is implanted with tumor cells and, after a subsequent period of time, injected with an antibody specific for an antigen expressed on the surface of the tumor cells. The isotype of the antibody is known prior to injection and the animals are analyzed for impairment of FcγR-dependent ADCC by comparison to ADCC observed in wild type animals.

In another aspect, mice deficient in endogenous low affinity receptors could be combined (e.g., by breeding) with other immune deficient mice to develop in vivo models of autoimmune disease. For example, Severe Combined Immunodeficiency (SCID) mice are routinely used in the art as model organisms for studying the immune system. SCID mice have an impaired ability to make T or B lymphocytes, or activate some components of the complement system, and cannot efficiently fight infections, reject tumors, and reject transplants. Low affinity FcγR α-subunit gene-deficient mice of the present invention may be bred to SCID mice to ascertain cell depletion in a host animal in response to administration of an antibody therapeutic (e.g., an anti-tumor antibody), which would determine the roles of ADCC and complement-dependent cytotoxicity (CDC) in tumor cell depletion in vivo.

In another aspect, genetically modified non-human animals comprising a replacement of the endogenous low affinity FcγR genes with low-affinity human FcγR genes are provided. Such animals are useful for studying the pharmacokinetics of fully human antibodies and hFcγR-mediated ADCC. In addition, human FcγR genes have been shown to exhibit polymorphisms or allelic variants associated with disease (e.g., SLE, RA, Wegener's granulomatosis, Guillain-Barré syndrome and Multiple Sclerosis). Thus, genetically modified non-human animals that comprise a replacement of the endogenous low affinity FcγR genes with specific allelic or polymorphic forms of human FcγR genes can be used to study human autoimmune diseases, and traits associated with the polymorphisms, in the animal. In a specific embodiment, the allelic forms of human FcγR genes are associated with enhanced efficacy for human IgG.

In another specific embodiment, the affect of a human low affinity FcγR polymorphism on the efficacy of a human antibody therapeutic is determined. In a specific embodiment, an anti-tumor antibody is administered to a first humanized mouse comprising a first polymorphism of a human FcγR and also to a second humanized mouse comprising a second polymorphism of a human FcγR, wherein the first and the second mice each comprise a human tumor cell; and the anti-tumor activity of the anti-tumor antibody is assessed in the first mouse and in the second mouse. In a specific embodiment, a treatment option is selected by a physician with respect to treating a human having the first or the second polymorphism and having a tumor corresponding to the human tumor cell, based on the assessment of efficacy of the anti-tumor antibody in the first mouse and in the second mouse.

Suitable polymorphisms of human FcγR genes include all those known in the art. For the human FcγRIIA gene, polymorphisms include, e.g., the high responder and low responder phenotype reported by the ability of T cells to proliferate in response to IgG. The high responder polymorphism is characterized by an arginine residue at position 131 (131Arg) while the low responder is characterized by a histidine residue at position 131 (131His). In a specific embodiment, the human FcγRIIA sequence comprises the 131His polymorphism. A representative protein sequence of the human FcγRIIA α-chain is shown in SEQ ID NO:32.

Single-nucleotide substitutions of the human FcγRIIB gene result in mis-sense substitutions in the ligand-binding domain (α-chain) and putatively affect the binding ability of an Fc portion of an IgG to bind to the α-chain of FcγRIIB on the cell surface. For example, substitution of a threonine residue for an isoleucine at position 232 (Ile232Thr) within the transmembrane domain of the FcγRIIB gene in mice has been shown to impair the signaling ability of the receptor. In a specific embodiment, the human FcγRIIB gene comprises the isoleucine variant (232Ile). A representative protein sequence of the human FcγRIIB α-chain is shown in SEQ ID NO:33.

Allelic variants of the human FcγRIIIA gene are proposed to be involved in susceptibility to SLE and RA. This allelic variant includes a phenylalanine substitution for valine at position 158 (Val158Phe). The valine allelic variant (158Val) is characterized to have a higher affinity for IgG1 and IgG3 than the phenylalanine allelic variant (158Phe). The 158Phe allelic variant has been proposed to lead to a reduced clearance of immune complexes. In a specific embodiment, the human FcγRIIIA gene comprises the 158Val allelic variant. A representative protein sequence of the human FcγRIIIA α-chain is shown in SEQ ID NO:35.

Allelic variants of the human FcγRIIIB gene include the neutrophil antigen 1 (NA1) and neutrophil antigen 2 (NA2) alleles. These allelic variants have been proposed to be involved in blood-transfusion reactions, alloimmune neutropaenia, SLE and Wegener's granulomatosis. The NA2 allelic variant is characterized by a diminished ability to mediate phagocytosis. In a specific embodiment, the human FcγRIIIB gene comprises the NA2 allelic variant. A representative protein sequence of the human FcγRIIIB α-chain is shown in SEQ ID NO:36.

In one aspect, the genetically modified non-human animals are useful for optimizing FcγR-mediated functions triggered by the Fc portion of therapeutic antibodies. The Fc regions of antibodies can be modified by any method known in the art. For example, amino acid residues within the Fc portion (e.g., CH2 and CH3 domains) can be modified to selectively enhance the binding affinity to human FcγRIIIA. Thus, the resulting antibody should have enhanced FcγRIIIA-dependent ADCC. In a specific embodiment, an animal expressing human FcγRIIIA of the present invention is used to evaluate the enhanced ADCC ability of a modified human antibody by administering a modified human antibody to the animal, detecting (e.g., in vitro) antibody binding to FcγRIIIA-expressing cells and comparing the ADCC activity observed to the ADCC activity observed from that determined in a wild type animal.

EXAMPLES

Example 1

Generation of Low Affinity FcγR Gene Deficient Mice

A targeting construct for introducing a deletion of the endogenous low affinity mouse FcγR locus (described below) was constructed (FIG. 1).

The targeting construct was made using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6):652-659) to modify the Bacterial Artificial Chromosome (BAC) RP23-395f6 (Invitrogen). RP23-395f6 BAC DNA was modified to delete the endogenous low affinity FcγRIIB, FcγRIV and FcγRIII genes comprising the α-chain of each of the FcγRs.

Briefly, upstream and downstream homology arms were made employing primers mFcR 5-up-1 (5'-ACCAGGATAT GACCTGTAGA G; SEQ ID NO:1) and mFcR 3-up-1a (GTCCATGGGT AAGTAGAAAC A; SEQ ID NO:2), and mFcR 5-DN (ATGCGAGCTC ATGCATCTATG TCGGGTGCGG AGAAAGAGGT AATGCATTCT TGCCCAATAC TTAC; SEQ ID NO:3) and mFcR 3-DN (ACTCATGGAG CCTCAACAGG A; SEQ ID NO:4), respectively. These homology arms were used to make a cassette that deleted the α-chains of the endogenous low affinity FcγRIIB, FcγRIV and FcγRIII genes. The targeting construct included a loxed neomycin resistance gene comprising homology arms comprising sequence homologous to a 5' and a 3' region with respect to the endogenous locus. Genes and/or sequences upstream of the endogenous FcγRIIB gene and downstream of the endogenous FcγRIII gene (see FIG. 1) were unmodified by the targeting construct.

The targeted deletion was confirmed by polymerase chain reaction (PCR) using primers outside the deleted region and within the targeting construct. The upstream region of the deleted locus was confirmed by PCR using primers to mFcR-up-detect (ATCCTGAGTA TACTATGACA AGA; SEQ ID NO:5) and PGK-up-detect (ACTAGTGAGA CGTGCTACTT C; SEQ ID NO:6), whereas the downstream region of the deleted locus was confirmed using primers pA-DN-detect (CTCCCACTCA TGATCTATAG A; SEQ ID NO:7) and mFcR-DN-detect (TGGAGCCTCA ACAGGACTCC A; SEQ ID NO:8). The nucleotide sequence across the upstream deletion point included the following, which indicates endogenous mouse sequence downstream of the FcγRIIB gene (contained within the parentheses below) linked contiguously to cassette sequence present at the deletion point: (GTCCATGGGT AAGTAGAAAC A)TTCGCTACC TTAGGACCGT TA (SEQ ID NO:9). The nucleotide sequence across the downstream deletion point included the following, which indicates cassette sequence contiguous with endogenous mouse sequence upstream of the FcγRIII gene (contained within the parentheses below): CGGGTGCGGA GAAAGAGGTA AT(GCATTCT GCCCAATACT TA) (SEQ ID NO:10).

Mice deficient in FcγRIIB, FcγRIII and FcγRIV were generated through electroporation of a targeted BAC DNA (described above) into mouse ES cells. Positive ES cells clones are confirmed by Taqman™ screening and karyotyping. Positive ES cell clones were then used to implant female mice to give rise to a litter of pups deficient in low affinity FcγR genes.

Example 2

Characterization of Low Affinity FcγR Gene Deficient Mice

Spleens were harvested from FcγR deficient and wild type mice and perfused with 10 mL Collagenase-D in sterile disposable bags. Each bag containing a single spleen was then placed into a Stomacher® (Seward) and homogenized at a medium setting for 30 seconds. Homogenized spleens were transferred to 10 cm petri dishes and incubated for 25 minutes at 37° C. Cells were separated with a pipette using a 1:50 dilution of 0.5 M EDTA, followed by another incubation for five minutes at 37° C. Cells were then pelleted with a centrifuge (1000 rpm for 10 minutes) and red blood cells were lysed in 4 mL ACK buffer (Invitrogen) for three minutes. Splenocytes were diluted with RPMI-1640 (Sigma) and centrifuged again. Pelleted cells were resuspended in 10 mL RPMI-1640 and filtered with a 0.2 μm cell strainer.

Figure 2:
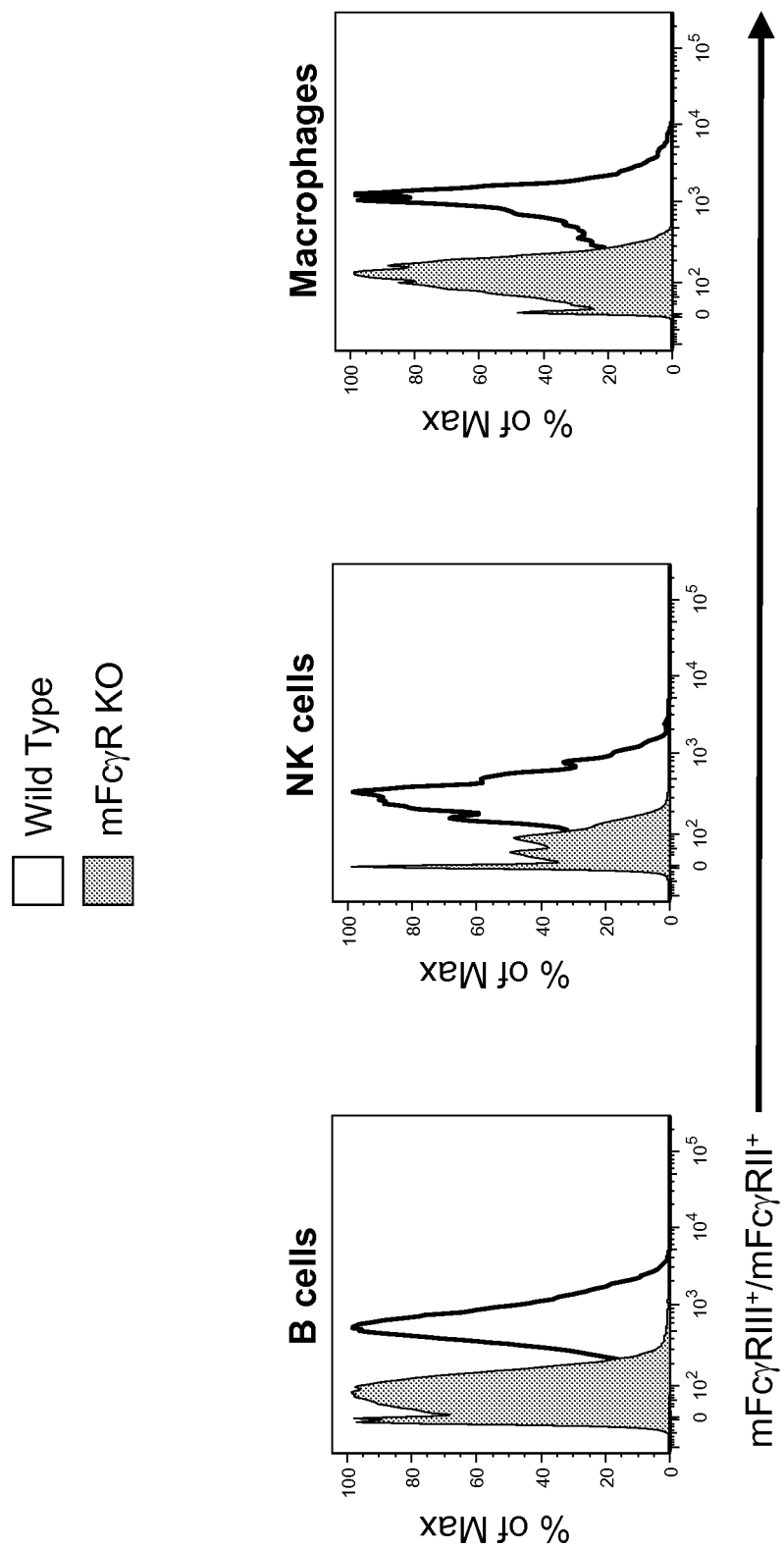
FIG. 2 shows histograms of splenocytes gated for B cells (anti-CD19), NK cells (anti-NKp46) and macrophages (anti-F4/80) including expression of endogenous mFcγRII and mFcγRIII genes for wild type and low affinity FcγR α-chain gene-deficient mice (mFcγR KO).
Figure 3A:
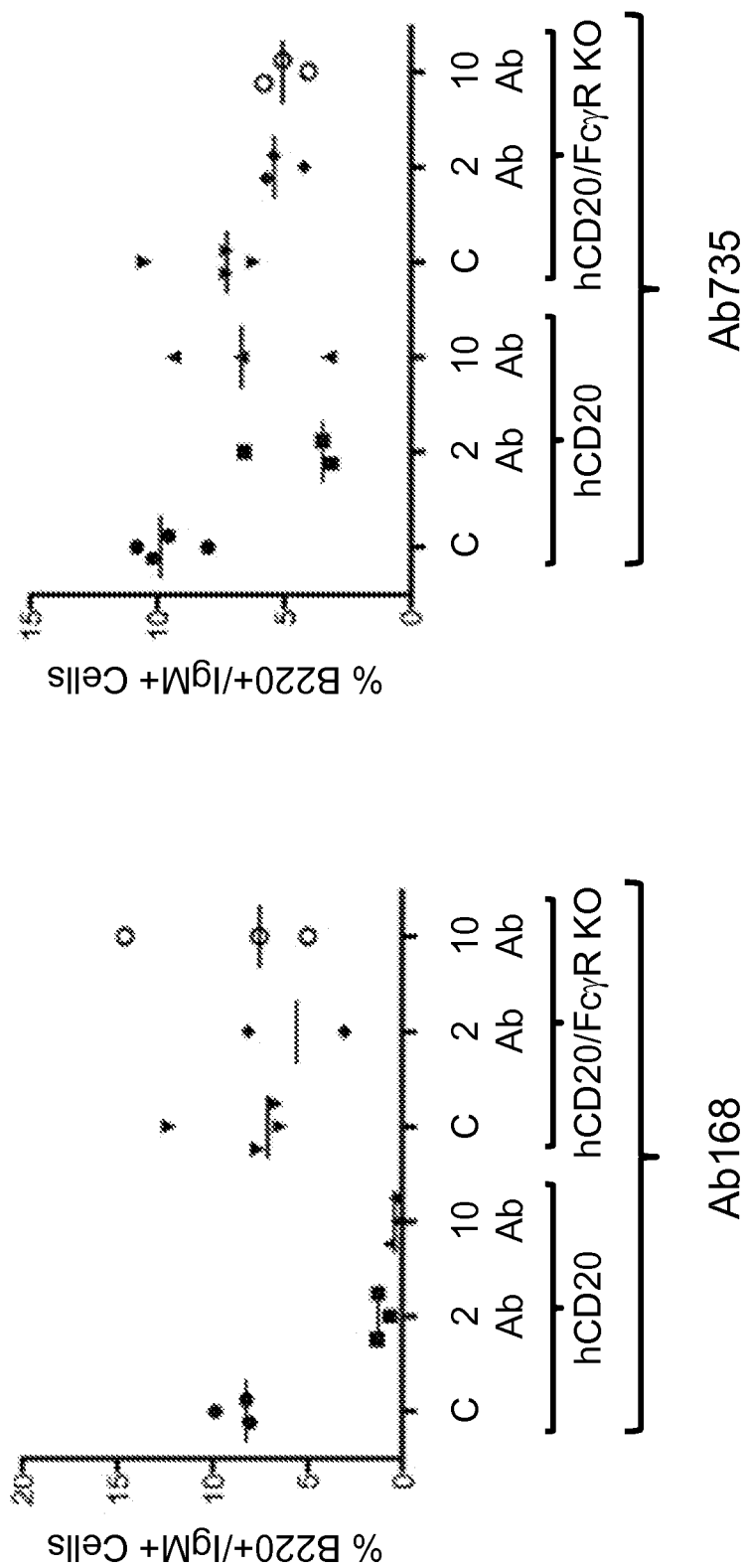
FIGS. 3A-3D show in vivo depletion of B cells with a human anti-human CD20 antibody with mouse Fc (Ab 168) or human Fc (Ab 735) in humanized CD20 mice (hCD20) and humanized CD20 mice bred to FcγR knockout mice (hCD20/FcγR KO) in several lymphocyte compartments: bone marrow (FIG. 3A), blood (FIG. 3B), lymph node (FIG. 3C) and spleen (FIG. 3D). For each graph, the y-axis shows the percent of gated B cells (B220$^+$/IgM$^+$ or B220$^+$/CD19$^+$) and the x-axis shows the antibody dose for each animal group: 10 mg/kg Control antibody (C), 2 mg/kg human anti-human CD20 antibody (2 Ab) and 10 mg/kg human anti-human CD20 antibody (10 Ab).
Figure 3B:
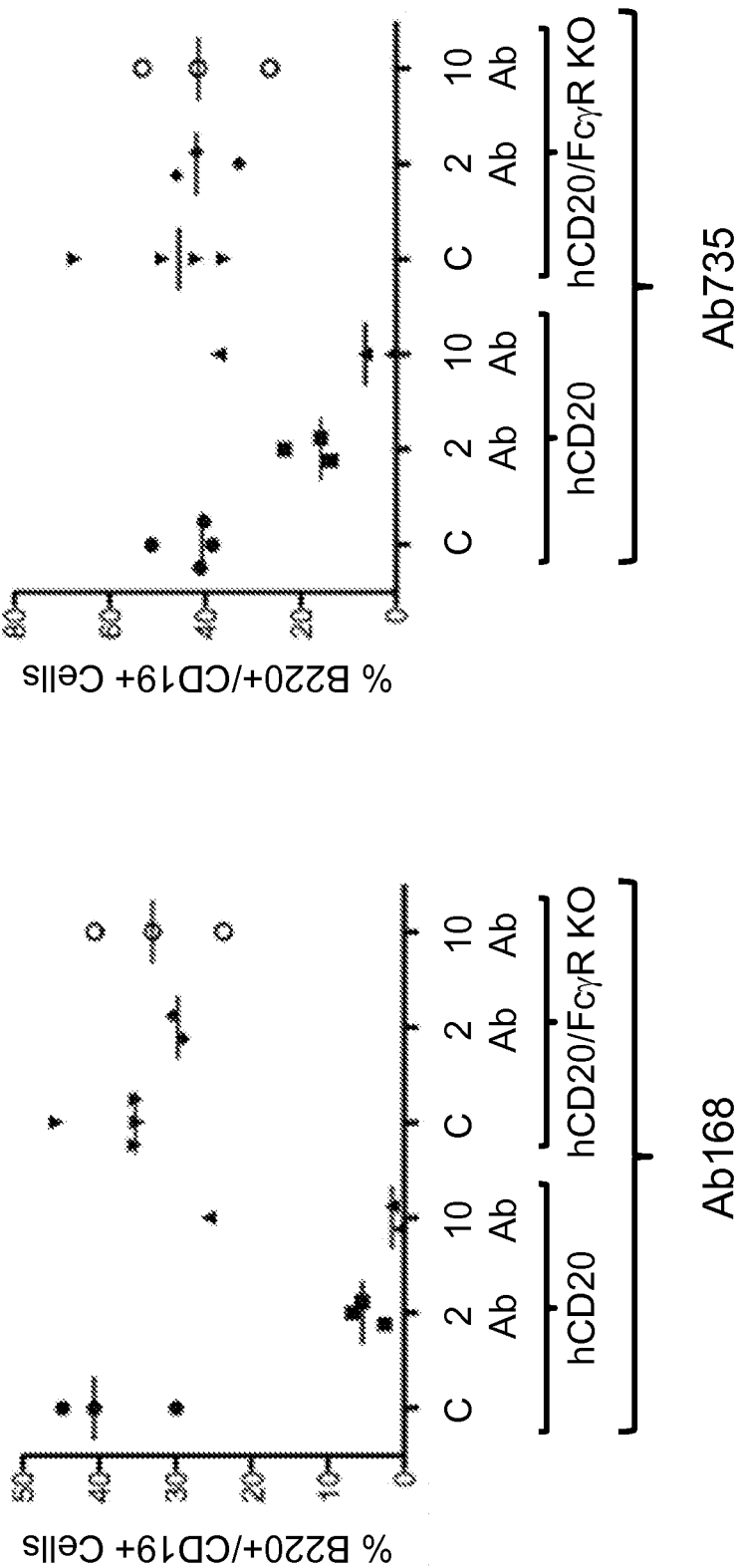
Figure 3C:
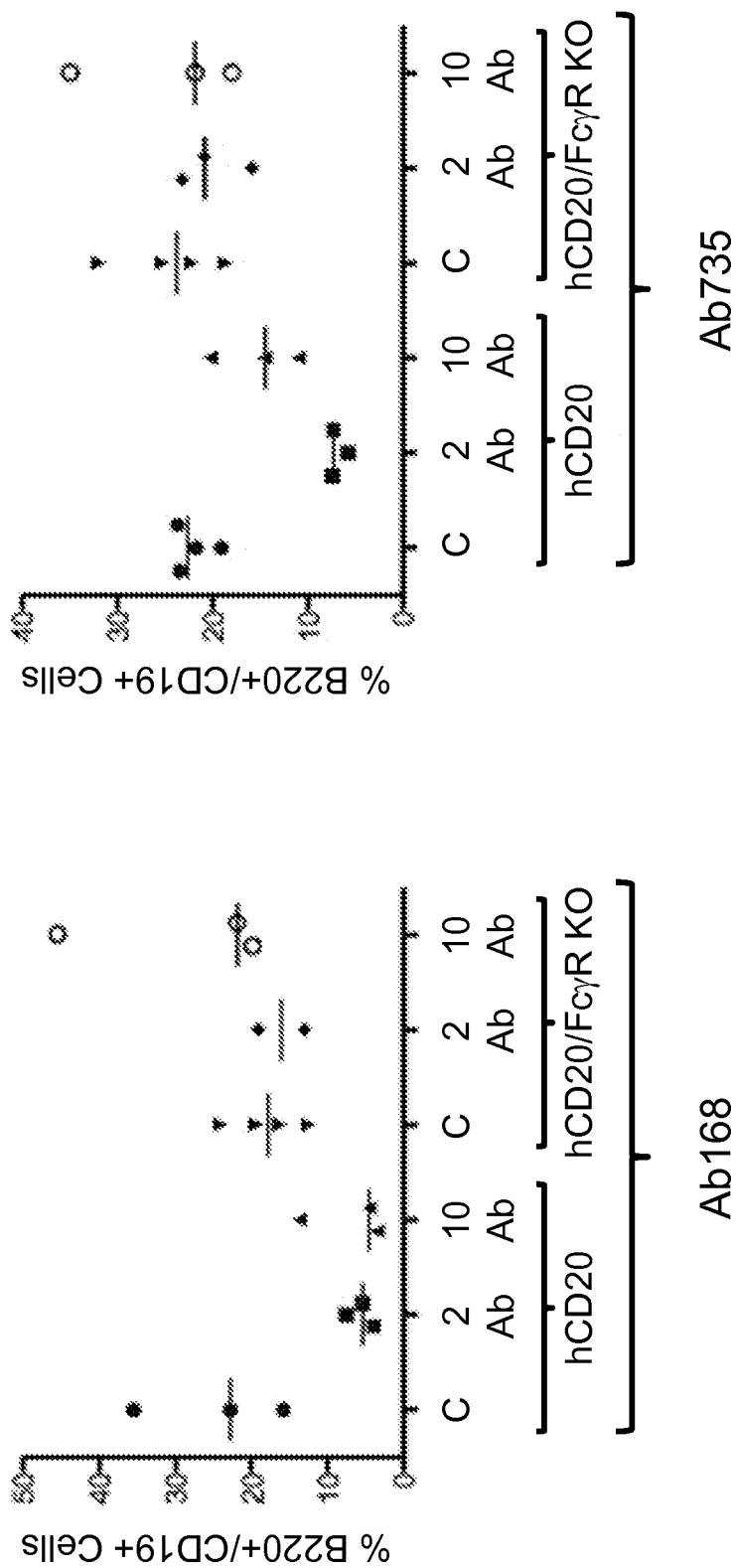
Figure 3D:
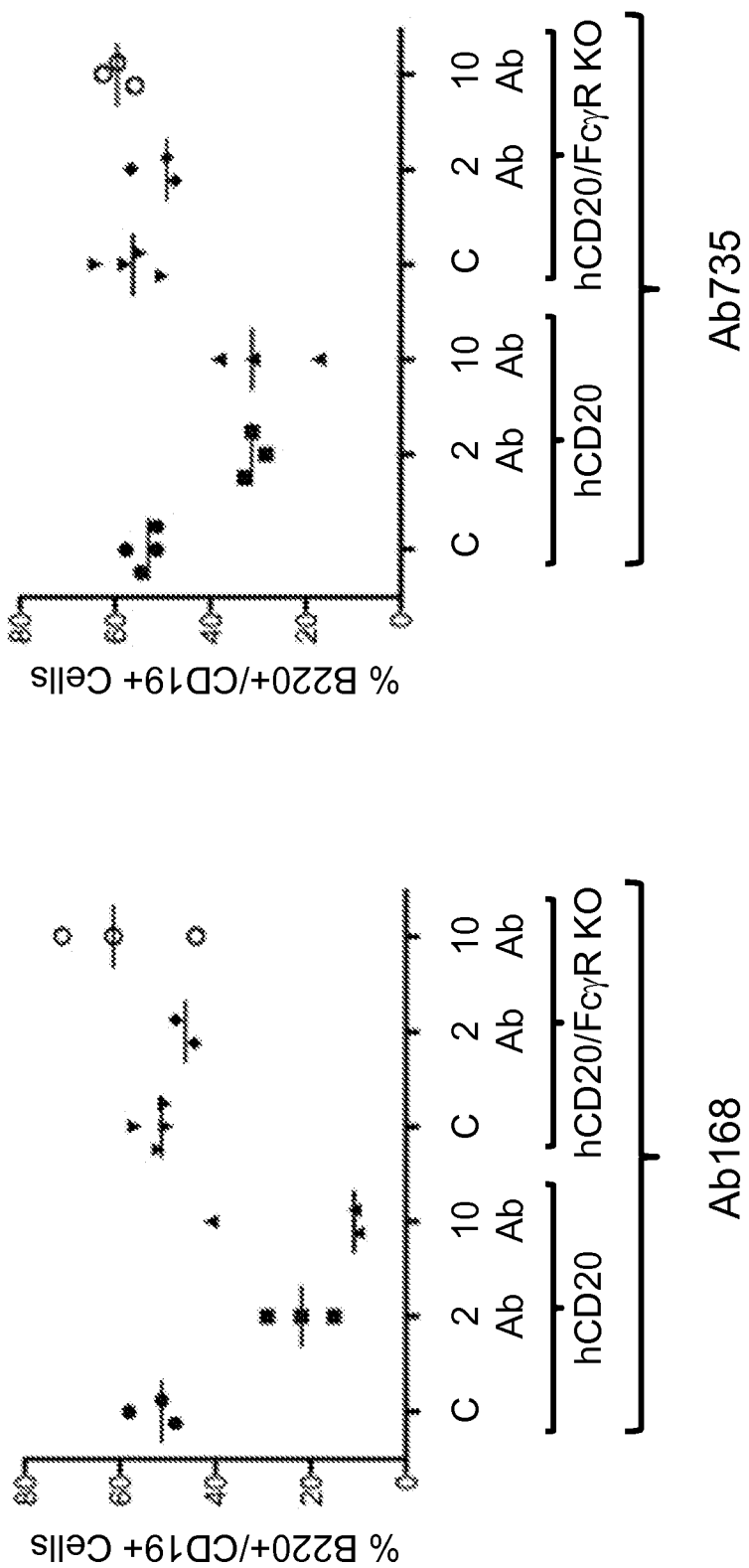

Flow Cytometry. Lymphocyte cell populations were identified by FACs on the BD LSR II System (BD Bioscience) with the following flourochrome conjugated cell surface markers: anti-CD19 (B cells), anti-CD3 (T cells), anti-NKp46 (NK cells) and anti-F4/80 (macrophages). Lymphocytes were gated for specific cell lineages and analyzed for expression of endogenous FcγRIII and FcγRIIB with a rat anti-mouse FcγRIII/II antibody (clone 2.4G2, BD Biosciences). Clone 2.4G2 recognizes a common polymorphic epitope on the extracellular domains of murine FcγRIII and FcγRII. The results show that there was no detectable murine low affinity FcγRIII or FcγRII on B-cells, NK cells and macrophages in mFcγR KO mice (FIG. 2).

ADCC Assay. Splenocytes isolated from FcγR gene deficient and wild type mice were analyzed for their ability to perform ADCC in a cell-killing assay. Cell populations were isolated and separated using MACS® Technology (Miltenyi Biotec). Briefly, T-cells were depleted from splenocytes using magnetically labeled anti-mouse CD3 beads. The T-cell depleted splenocytes were then enriched for NK cells using magnetically labeled anti-mouse CD49B beads. Separately, Raji cells (expressing human CD20) were coated with varying concentrations (ranging from 0.1 to 10 μg/mL) of mouse anti-human CD20 antibody (Clone B1; Beckman Coulter) for 30 minutes at 4° C. The antibody-coated Raji cells were incubated with the enriched NK cells at ratios (NK:Raji) of 100:1 and 50:1 for four hours at 37° C. Cell death was measured using the CytoTox-Glo™ Cytotoxicity Assay (Promega). Luminescence signal is derived from lysed cells and proportional to the number of dead cells. Luminescence from controls (no anti-CD20 antibody) was determined for background dead cell count for each ratio and subtracted from measurements for wild type and KO mice. Average cell death was calculated and percent decrease in cell killing (% ADCC) was determined by comparison to wild type. Results are shown in Table 1.

TABLE 1

| | | % ADCC | | |
|---|---|---|---|---|
| | mFcγR KO | 10 μg/mL B1 Antibody | 1 μg/mL B1 Antibody | 0.1 μg/mL B1 Antibody |
| NK cell:Raji cell | 100:1 | 42 | 53 | 35 |
| | 50:1 | 15 | 0 | 0 |

Example 3

In Vivo Depletion of B Cells in Low Affinity FcγR Gene Deficient Mice

The effect of human or murine Fc isotypes on B cell depletion through the ADCC pathway was determined for various B cell compartments in low affinity FcγR gene deficient mice engineered to express human CD20 using a human anti-human CD20 antibody. Mice expressing human CD20 were separately engineered using techniques known in the art. Mice that express human CD20 on B cells and deficient in low affinity FcγR genes (described in Example 1) were made by standard breeding techniques of the two engineered strains.

Separate groups of mice that expressed human CD20 and had a full complement of endogenous low affinity FcγR genes were each administered one of the following: (1) 10 mg/kg control antibody (N=4; human antibody not specific for human CD20 having a mouse IgG2a); (2) 2 mg/kg Ab 168 (N=3; human anti-hCD20 antibody with a mouse IgG2a; heavy and light chain variable region sequences found in SEQ ID NOs: 339 and 347, respectively, of US Patent Publication No. 2009/0035322); (3) 10 mg/kg Ab 168; (4) 2 mg/kg Ab 735 (N=3; Ab 168 with human IgG1); (5) 10 mg/kg Ab 735. In a similar set of experiments, groups of mice that expressed human CD20 and had a deletion of the endogenous low affinity FcγR genes were administered the control and human anti-hCD20 antibodies (described above).

Mice in each group were administered the antibodies by intra-peritoneal injections. Seven days post-injection, animals were euthanized and the remaining B cell contents of bone marrow (B220$^+$/IgM$^+$), peripheral blood (B220$^+$/CD19$^+$), lymph node (B220$^+$/CD19$^+$) and spleen (B220$^+$/CD19$^+$) were identified by multi-color FACS performed on a LSR-II flow cytometer and analyzed using Flow-Jo software (as described above). The results of the B cell depletion experiments are shown in FIGS. 3A-3D.

As shown in FIGS. 3A-3D, Ab 735 depleted B cells with a lower efficiency than Ab 168 in mice containing a complete complement of low affinity FcγR genes. Further, for both antibodies (mouse and human Fc), B cell depletion was significantly reduced in mice lacking a complete complement of low affinity FcγR genes. This Example shows that the ability to deplete B cells through the ADCC pathway requires low affinity FcγRs and demonstrate that measuring ADCC efficiency for antibodies containing human constant regions in mice is more suitable by the use of genetically engineered mice containing a full complement of human low affinity FcγR genes.

Example 4

Generation of FcγRIIIA/FcγRIIA Humanized Mice

A targeting construct for introducing two low affinity human FcγR genes into a deleted endogenous low affinity mouse FcγR locus (described below) was constructed (FIG. 4).

A targeting construct comprising human FcγRIIA and FcγRIIIA genes was made using similar methods (see Example 1) through modification of BAC RP23-395f6 and CTD-2514j12 (Invitrogen). BAC DNA of both BACs was modified to introduce a deletion of the α-chains of the low affinity human FcγRIIA and FcγRIIIA genes into the deleted endogenous low affinity FcγR locus.

In a similar fashion, upstream and downstream homology arms were made employing primers h14 (GCCAGCCACA AAGGAGATAA TC; SEQ ID NO:11) and h15 (GCAA-CATTTA GGACAACTCG GG; SEQ ID NO:12), and h4 (GATTTCCTAA CCACCTACCC C; SEQ ID NO:13) and h5 (TCTTTTCCAA TGGCAGTTG; SEQ ID NO:14), respectively. These homology arms were used to make a cassette that introduced the α-chains of low affinity human FcγRIIA and FcγRIIIA genes into the endogenous mouse low affinity FcγR locus. The targeting construct included a 5' homology arm including sequence 5' to the deleted endogenous low affinity FcγR locus, a FRT'ed hygromycin resistance gene, followed by a human genomic fragment from BAC CTD-2514j12 comprising low affinity human FcγRIIA and FcγRIIIA α-chain genes, and a 3' homology arm comprising mouse sequence 3' to the deleted endogenous low affinity FcγR locus (middle of FIG. 4). For a mouse that expresses FcγRIIA on mouse platelets, a targeting construct was made in a similar manner (using the same BACs) except that the construct comprises an extended promoter sequence operably linked to the human FcγRIIA gene in the human genome, e.g., up to about 18 kb or more, using a hygromycin cassette that is flanked on both sides by lox2372 sites, wherein the junction of the promoter region and the first lox 2372 site is ATCGGGGATA GAGATGTTTG (CC)GCGATCGC GGTACCGGGC (SEQ ID NO:37 human/lox2372 junction in parentheses) and wherein the junction of the second lox2372 site and mouse sequence is TTATACGAAG TTATACCGG(T G)CAT-TCTTGC CCAATACTTA (SEQ ID NO:38 lox2372/mouse junction in parentheses). Suitable primers were used to genotype the humanization comprising the promoter region.

Targeted insertion of the human FcγRIIA and FcγRIIIA α-chain genes was confirmed by PCR (as described above). The upstream region of the partially humanized locus was confirmed by PCR using primers h16 (CCCAGGTAAG TCGTGATGAA ACAG; SEQ ID NO:15) and pA-DN-detect (CTCCCACTCA TGATCTATAG A; SEQ ID NO:16), whereas the downstream region of the partially humanized locus was confirmed using primers mFcR DN-detect-9 (TGGAGCCTCA ACAGGACTCC A; SEQ ID NO:17) and h6 (CACACATCTC CTGGTGACTT G; SEQ ID NO:18). The nucleotide sequence across the downstream junction included the following, which indicates a novel insertion point of endogenous human sequence upstream of the hFcγRIIA gene (contained within the parentheses below) contiguous with endogenous mouse sequence 3' of the deleted low affinity FcγR locus: (CAACTGCCAT TGGAAAAGA)C TCGAGTGCCA TTTCATTACC TC (SEQ ID NO:19). The upstream junction includes two novel sequences. One point of the upstream junction includes the following, which indicates nucleotide sequence of the hygromycin cassette contiguous with human genomic sequence (contained within the parentheses below) that comprises the upstream region of the inserted hFcγRIIIA gene: TAAACCCGCG GTGGAGCTC(G CCAGCCACAA AGGAGATAAT CA) (SEQ ID NO:20). The second point of the upstream junction includes the following, which indicates a nucleotide sequence of an endogenous mouse sequence (contained within the parentheses below) from the upstream region of the deleted low affinity FcγR locus contiguous with a nucleotide sequence within the hygromycin cassette: (CCATGGGTAA GTAGAAAC)TC TAGACCCCCG GGCTCGATAA CT (SEQ ID NO:21).

Mice containing two low affinity human FcγR genes (hFcγRIIA, lacking extended promoter region, and hFcγRIIIA) in place of the endogenous low affinity mouse FcγR locus were generated through electroporation of the targeted BAC DNA (described above) into mouse ES cells. Positive ES cells clones were confirmed by Taqman™ screening and karyotyping. Positive ES cell clones were then used to implant female mice using the VELOCI-MOUSE® method (described below) to generate a litter of pups containing a replacement of the endogenous low affinity FcγR genes with the two human low affinity FcγR genes.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99. VELOCIMICE® (F0 mice fully derived from the donor ES cell) bearing hFcγRIIA and hFcγRIIIA were identified by genotyping using a modification of allele assay (Valenzuela et al., supra) that detected the presence of the hFcγR genes.

Mice bearing the hFcγR genes can be bred to a Cre deleter mouse strain (see, e.g., International Patent Application Publication No. WO 2009/114400) in order to remove any loxed neo cassette introduced by the targeting construct that is not removed, e.g., at the ES cell stage or in the embryo. Optionally, the neomycin cassette is retained in the mice.

Pups are genotyped and a pup heterozygous for the hFcγR genes is selected for characterizing FcγRIIA and FcγRIIIA humanizations.

Example 5

Characterization of FcγRIIIA/FcγRIIA Humanized Mice

Spleens were harvested from humanized FcγRIIIA/FcγRIIA (heterozygotes, lacking the extended FcγRIIA promoter region) and wild type mice and prepared for FACs (as described above).

Flow Cytometry. Lymphocytes were gated for specific cell lineages and analyzed for expression of hFcγRII and hFcγRIII using a mouse anti-human FcγRII antibody (Clone FLI8.26; BD Biosciences) and a mouse anti-human FcγRIII antibody (Clone 3G8; BD Biosciences), respectively. Relative expression (++, +) or no expression (−) observed for each lymphocyte subpopulation is shown in Table 2.

TABLE 2

| Lymphocyte Lineage | hFcγRIII | hFcγRII |
| --- | --- | --- |
| B cells | − | − |
| NK cells | ++ | − |
| Macrophages | + | + |
| Neutrophils | − | + |

Figure 5A:
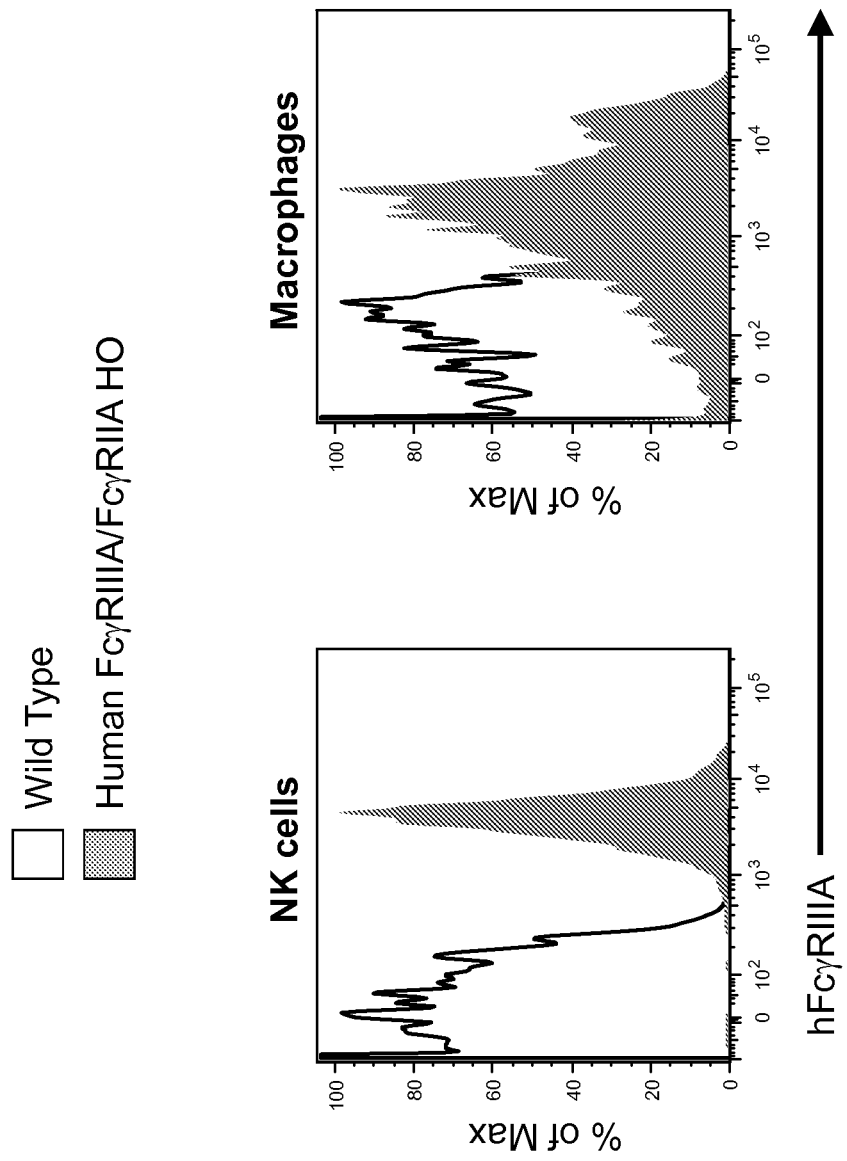
FIG. 5A shows histograms of splenocytes gated for NK cells (anti-NKp46) and macrophages (anti-F4/80) including expression of human FcγRIIIA for wild type and human FcγRIIIA-IIA homozygote mice (Human FcγRIIIA/FcγRIIA HO).
Figure 5B:
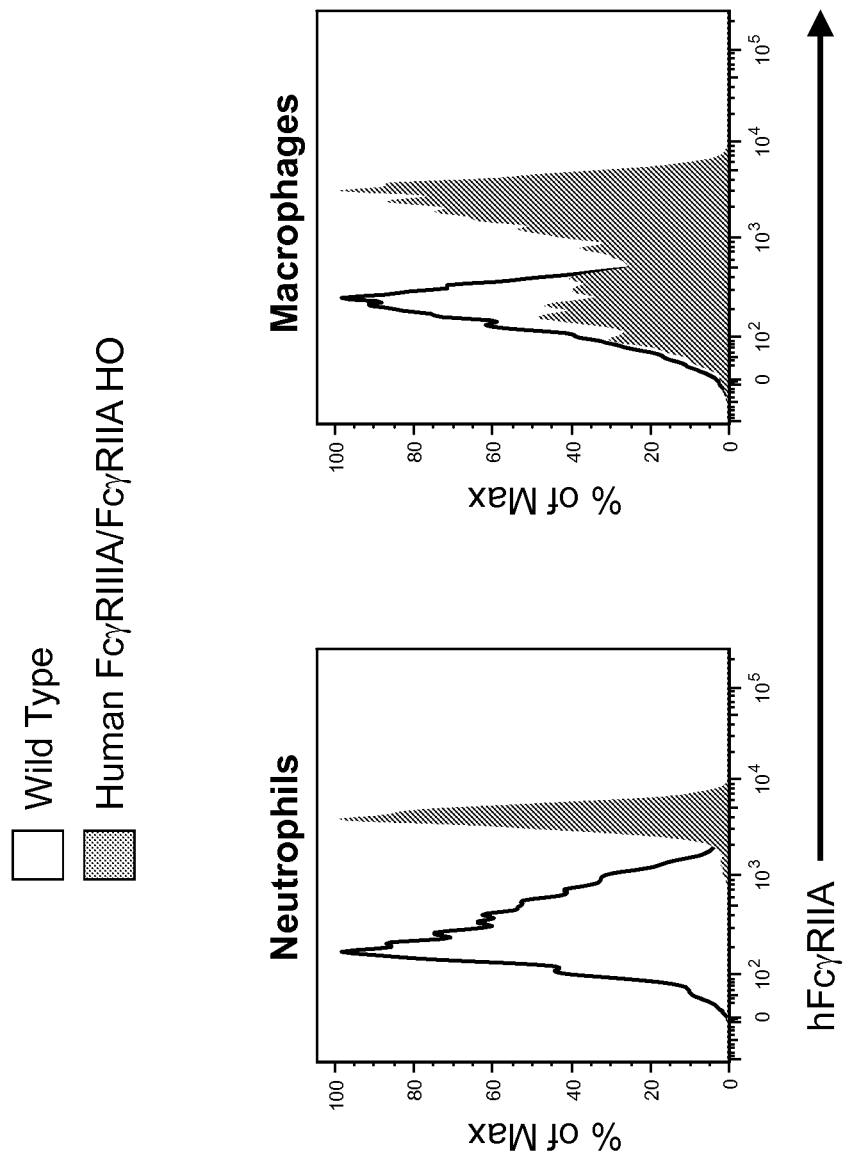
FIG. 5B shows histograms of splenocytes gated for neutrophils (anti-Ly6G) and macrophages (anti-F4/80) including expression of human FcγRIIA for wild type and human FcγRIIIA-IIA homozygote mice (Human FcγRIIIA/FcγRIIA HO).

In a similar experiment, spleens were harvested from humanized FcγRIIIA/FcγRIIA (homozygotes, lacking the extended FcγRIIA promoter region) and wild type mice and prepared for FACs (as described above). Results are shown in FIGS. 5A and 5B. Percent of separate lymphocyte cell populations expressing human FcγRIIIA, FcγRIIA or both in FcγRIIIA/FcγRIIA homozygote mice is shown in Table 3.

TABLE 3

| Lymphocyte Lineage | hFcγRIII | hFcγRII | hFcγRII/hFcγRIII |
|---|---|---|---|
| NK cells | 97 | — | — |
| Macrophages | 26 | 14 | 39 |
| Neutrophils | — | 94 | — |

As shown in this Example, genetically modified mice (both heterozygote and homozygote genotypes) generated in accordance with Example 3 expressed human FcγRIIIA on NK cells and macrophages; and human FcγRIIA on neutrophils and macrophages, but not platelets. Human FcγRIIIA was highly expressed on NK cells. The expression pattern of human FcγR genes shown in this Example is consistent with the expression patterns of these genes in human accessory cells.

Example 6

Generation of Low Affinity FcγR Humanized Mice

A targeting construct for introducing three additional low affinity human FcγR genes into a partially humanized endogenous low affinity FcγR locus (described below) was constructed (FIG. 6).

A targeting construct comprising human FcγRIIB, FcγRIIIB and FcγRIIC genes was made using similar methods (see Example 1) through modification of BAC RP-23 395f6 and RP-11 697e5 (Invitrogen). BAC DNA of both BACs was modified to introduce the α-chains of the low affinity human FcγRIIB, FcγRIIIB and FcγRIIC genes into the partially humanized endogenous low affinity FcγR locus containing two human low affinity FcγR genes.

In a similar fashion, upstream and downstream homology arms were made employing primers mFcR up-1 (ACCAGGATAT GACCTGTAGA G; SEQ ID NO:22) and mFcR2b NheI-2 (GTTTCTACTT ACCCATGGAC; SEQ ID NO:23), and h10 (AAATACACAC TGCCACAGAC AG; SEQ ID NO:24) and h11 (CCTCTTTTGT GAGTTTCCTG TG; SEQ ID NO:25), respectively. These homology arms were used to make a cassette that introduced DNA sequences encoding the α-chains of low affinity human FcγRIIB, FcγRIIIB and FcγRIIC. The targeting construct included a 5′ homology arm including mouse sequence 5′ to the deleted endogenous low affinity FcγR locus, a loxed neomycin resistance gene, followed by a human genomic fragment from BAC RP-11 697e5 comprising low affinity human FcγRIIB, FcγRIIIB and FcγRIIC α-chain genes, and a 3′ homology arm comprising human sequence 5′ to the low affinity human FcγRIIIA α-chain gene (middle of FIG. 6).

Targeted insertion of three additional low affinity human FcγR genes was confirmed by PCR (as described above). The upstream region of the fully humanized locus was confirmed by PCR using primers mFcR up-detect-3 (GAGTATACTA TGACAAGAGC ATC; SEQ ID NO:26) and PGK up-detect (ACTAGTGAGA CGTGCTACTT C; SEQ ID NO:27), whereas the downstream region of the fully humanized locus was confirmed using primers neo detect (CTCCCACTCA TGATCTATAG A; SEQ ID NO:28) and h12 (CTTTTTATGG TCCCACAATC AG; SEQ ID NO:29). The nucleotide sequence across the downstream junction included the same human genomic sequence upstream of the hFcγRIIA α-chain gene (see Example 3; SEQ ID NO:19). The nucleotide sequence across the upstream junction included the following, which indicates two novel junctions of mouse and cassette sequences and cassette and human genomic sequences at the insertion point. The junction of genomic mouse sequence (contained within the parentheses below) and the upstream region of the neo cassette sequence is: (GTCCATGGGT AAGTAGAAAC A)TTCGCTACC TTAGGACCGT TA (SEQ ID NO:30). The second novel junction includes the joining of the 3′ end of neo cassette (contained within the parentheses below) and a human genomic sequence downstream of the hFcgRIIB α-chain gene: (GCTTATCGAT ACCGTCGAC)A AATACACACT GCCACAGACA GG; SEQ ID NO:31). These junctions are show in FIG. 6 (middle) within the targeting construct. The resulting modified genome of the fully humanized low affinity FcγR locus is shown in FIG. 6 (bottom).

Mice containing five low affinity human FcγR genes in place of the endogenous low affinity mouse FcγR locus were generated through electroporation of the targeted BAC DNA (described above) into mouse ES cells. Positive ES cells clones were confirmed by Taqman™ screening and karyotyping. Positive ES cell clones were then used to implant female mice (as described above) to give rise to a litter of pups containing a replacement of the endogenous low affinity FcγR genes for five human low affinity FcγR genes.

Example 7

Characterization of Low Affinity FcγR Humanized Mice

Spleens were harvested from fully humanized FcγR (heterozygotes) and wild type mice and prepared for FACs (as described above).

Flow Cytometry. Lymphocytes were gated for specific cell lineages and analyzed for expression of human FcγRIIA and FcγRIIIA using a mouse anti-human FcγRII antibody (Clone FLI8.26; BD Biosciences) and a mouse anti-human FcγRIII antibody (Clone 3G8; BD Biosciences), respectively. Relative expression (++, +) or no expression (−) observed for each lymphocyte subpopulation is shown in Table 4.

TABLE 4

| Lymphocyte Lineage | hFcγRIII | hFcγRII |
|---|---|---|
| B cells | − | + |
| NK cells | + | + |
| Macrophages | + | + |
| Neutrophils | + | + |

Figure 7:
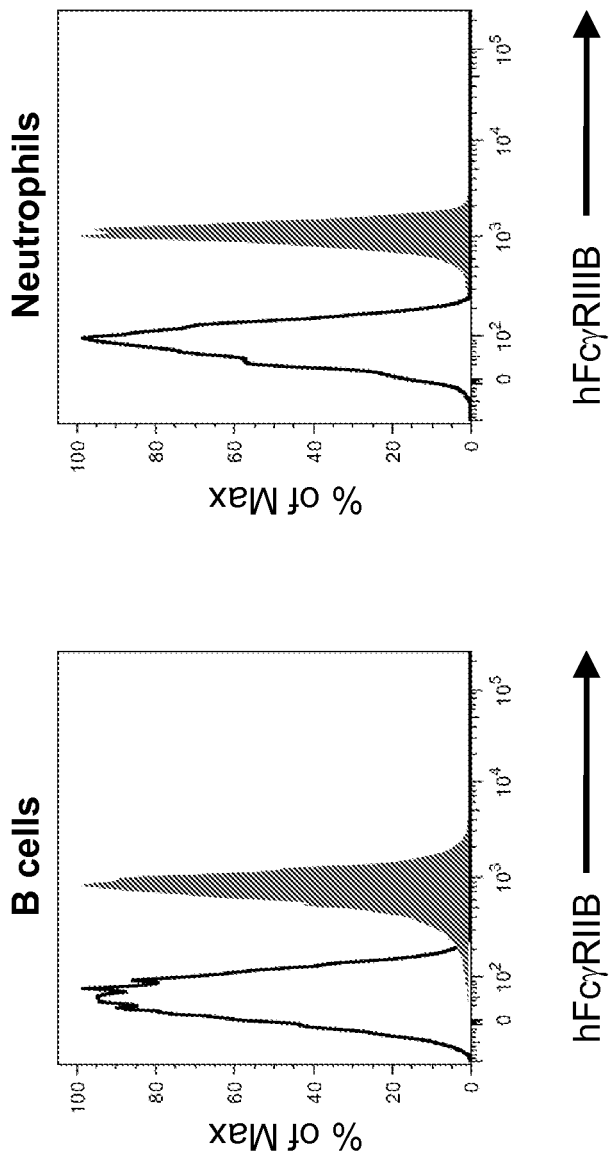
FIG. 7 shows histograms of splenocytes gated for B cells (anti-CD19) and neutrophils (anti-Ly6G) including expression of human FcγRIIB and human FcγRIIIB for wild type and human FcγRIIIA-IIIB-IIA-IIB-IIC homozygote mice (Human FcγRIIIA/FcγRIIIB/FcγRIIA/FcγRIIB/FcγRIIC HO).

In a similar experiment, spleens were harvested from fully humanized FcγR (homozygotes) and wild type mice and prepared for FACs (as described above). Results are shown in FIG. 7. Percent of separate lymphocyte cell populations expressing human FcγRIIIA, human FcγRIIIB, human FcγRIIA, human FcγRIIB, human FcγRIIC or a combination thereof in fully humanized FcγR homozygote mice is shown in Table 5.

TABLE 5

| Lymphocyte Lineage | hFcγRIII | hFcγRII | hFcγRII/hFcγRIII |
|---|---|---|---|
| B cells | — | 100 | — |
| NK cells | 30 | — | — |
| Macrophages | <1 | 55 | 26 |
| Neutrophils | — | 100 | — |

As shown in this Example, genetically modified mice (both heterzygote and homozygote genotypes) generated in accordance with Example 5 expressed human FcγRIIIA on NK cells and macrophages, human FcγRIIIB on neutrophils, human FcγRIIA on neutrophils and macrophages, human FcγRIIB on B cells, and human FcγRIIC on NK cells. The expression pattern of human FcγR genes shown in this Example is consistent with the expression patterns of these genes in human accessory cells.

Example 8

ADCC in Humanized FcγR Mice

Splenocytes isolated from FcγR gene deficient (i.e. knockout), FcγRIIIA/FcγRIIA (homozygotes), FcγRIIIA/FcγRIIIB/FcγRIIA/FcγRIIB/FcγRIIC (homozygotes) and wild type mice were analyzed for their ability to perform ADCC in a cell-killing assay (as described above in Example 2).

Briefly, cell populations were isolated and separated using MACS® Technology (Miltenyi Biotec). Briefly, T and B cell depleted splenocytes were cultured for two weeks in the presence of mouse IL-2 (500 U/mL). The resulting expanded NK cells were used as effector cells in the ADCC assays at a ratio of 50:1 (NK:Raji). Raji cells were coated with 10 ug/mL of Ab 168 or Ab 735 (as described above in Example 3). Results are shown in Table 6.

TABLE 6

| NK Cell Genotype | % ADCC | |
| --- | --- | --- |
| | 10 µg/mL Ab 168 | 10 µg/mL Ab 735 |
| Wild Type | 89 | 72 |
| Mouse FcγR KO | 13 | 14 |
| Human FcγRIIIA-IIA HO | 78 | 85 |
| Human FcγRIIIA-IIIB-IIA-IIB-IIC HO | 81 | 59 |

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

We claim:

1. A mouse lymphocyte having a genome that comprises at least one human low affinity FcγR α-chain gene encoding a human low affinity FcγR α-chain with a polymorphism, wherein the human low affinity FcγR α-chain gene replaces an endogenous low affinity FcγR α-chain gene, and wherein the mouse lymphocyte comprises a functional endogenous FcR γ-chain and functionally expresses the human low affinity FcγR α-chain gene.

2. The mouse lymphocyte of claim 1, wherein the human low affinity FcγR α-chain is a low affinity FcγRIIA α-chain.

3. The mouse lymphocyte of claim 2, wherein the polymorphism is a 131His polymorphism.

4. The mouse lymphocyte of claim 2, wherein the polymorphism is a 131Arg polymorphism.

5. The mouse lymphocyte of claim 1, wherein the human low affinity FcγR α-chain is a low affinity FcγRIIB α-chain.

6. The mouse lymphocyte of claim 5, wherein the polymorphism is a 232Ile polymorphism.

7. The mouse lymphocyte of claim 5, wherein the polymorphism is a 232Thr polymorphism.

8. The mouse lymphocyte of claim 1, wherein the human low affinity FcγR α-chain is a low affinity FcγRIIIA α-chain.

9. The mouse lymphocyte of claim 8, wherein the polymorphism is a 158Val polymorphism.

10. The mouse lymphocyte of claim 8, wherein the polymorphism is a 158Phe polymorphism.

11. The mouse lymphocyte of claim 1, wherein the mouse lymphocyte is a mouse natural killer (NK) cell, a mouse B cell, or a mouse T cell.

12. A mouse embryonic stem (ES) cell having a genome that comprises at least one human low affinity FcγR α-chain gene encoding a human low affinity FcγR α-chain with a polymorphism, wherein the human low affinity FcγR α-chain gene replaces an endogenous low affinity FcγR α-chain gene, and wherein the mouse ES cell comprises a functional endogenous FcR γ-chain gene.

13. The mouse ES cell of claim 12, wherein the human low affinity FcγR α-chain is a low affinity FcγRIIA α-chain.

14. The mouse ES cell of claim 13, wherein the polymorphism is a 131His polymorphism.

15. The mouse ES cell of claim 13, wherein the polymorphism is a 131Arg polymorphism.

16. The mouse ES cell of claim 12, wherein the human low affinity FcγR α-chain is a low affinity FcγRIIB α-chain.

17. The mouse of claim 16, wherein the polymorphism is a 232Ile polymorphism.

18. The mouse of claim 16, wherein the polymorphism is a 232Thr polymorphism.

19. The mouse ES cell of claim 12, wherein the human low affinity FcγR α-chain is a low affinity FcγRIIIA α-chain.

20. The mouse ES cell of claim 19, wherein the polymorphism is a 158Val polymorphism.

21. The mouse ES cell of claim 19, wherein the polymorphism is a 158Phe polymorphism.

22. A mouse embryo comprising the mouse ES cell of claim 12.

23. A method of testing an agent comprising an Fc region of a human antibody, the method comprising:
   (a) administering an agent comprising an Fc region of a human antibody to a genetically modified mouse whose genome comprises at least one human low affinity FcγR α-chain gene encoding a human low affinity FcγR α-chain with a polymorphism, wherein the human low affinity FcγR α-chain gene replaces an endogenous low affinity FcγR α-chain gene, wherein the mouse comprises a functional endogenous FcR γ-chain and functionally expresses the human low affinity FcγR α-chain gene, wherein the agent comprising an Fc region of a human antibody binds to a target cell in the mouse; and
   (b) measuring the cell-mediated immunity elicited by the agent comprising an Fc region of a human antibody in the mouse.

24. The method of claim 23, wherein the cell-mediated immunity elicited by the agent comprising an Fc region of a human antibody is measured in a blood sample of the mouse.

25. The method of claim 23, wherein the human low affinity FcγR α-chain is a low affinity FcγRIIA α-chain.

26. The method of claim 25, wherein the polymorphism is a 131His polymorphism.

27. The method of claim 25, wherein the polymorphism is a 131Arg polymorphism.

28. The method of claim 23, wherein the human low affinity FcγR α-chain is a low affinity FcγRIIB α-chain.

29. The method of claim 28, wherein the polymorphism is a 232Ile polymorphism.

30. The method of claim 28, wherein the polymorphism is a 232Thr polymorphism.

31. The method of claim 23, wherein the human low affinity FcγR α-chain is a low affinity FcγRIIIA α-chain.

32. The method of claim 31, wherein the polymorphism is a 158Val polymorphism.

33. The method of claim 31, wherein the polymorphism is a 158Phe polymorphism.

\* \* \* \* \*